United States Patent [19]
Hasegawa et al.

[11] Patent Number: 6,046,218
[45] Date of Patent: Apr. 4, 2000

[54] PYRIDINE DERIVATIVE AND MEDICAMENT CONTAINING THE SAME AS AN EFFECTIVE INGREDIENT

[75] Inventors: Hiroshi Hasegawa, Sakura; Tadashi Mikami, Sawara; Koichi Tachibana, Narita; Kazuo Yamazaki, Sawara; Noriyuki Kawamoto, Narita; Noriaki Shioiri, Narita; Koji Kusano, Narita; Susumu Sato, Narita; Hideaki Matsuda, Abiko; Toshio Yokoyama, Tokyo, all of Japan

[73] Assignee: SS Pharmaceutical Co., Ltd., Tokyo, Japan

[21] Appl. No.: 08/952,072

[22] PCT Filed: Mar. 7, 1997

[86] PCT No.: PCT/JP97/00712

§ 371 Date: Nov. 17, 1997

§ 102(e) Date: Nov. 17, 1997

[87] PCT Pub. No.: WO97/33870

PCT Pub. Date: Sep. 18, 1997

[30] Foreign Application Priority Data

Mar. 15, 1996 [JP] Japan ................................. 8-058906

[51] Int. Cl.[7] .................. A61K 31/435; A61K 31/44; C07D 211/72
[52] U.S. Cl. .................. 514/348; 514/277; 514/885; 546/296
[58] Field of Search .................. 514/277, 885, 514/348; 546/296

[56] References Cited

FOREIGN PATENT DOCUMENTS

| 0 462 800 | 12/1991 | European Pat. Off. . |
| 59-225171 | 12/1984 | Japan . |
| 61-27168 | 12/1986 | Japan . |
| 1-290683 | 11/1989 | Japan ................. C07D 519/00 |
| 6-508125 | 9/1994 | Japan . |

OTHER PUBLICATIONS

Chemical Abstract, Nakagawa, S., et al., "(Quinoliziniumyl)thiomethylcephems as antibacterial agents and their preparation," vol. 113, No. 3, (Jul. 16, 1990) XP002100713.

Chemical Abstracts 12th Collective Index, pp. 16012F, 16168F XP002100712.

Haeney, "The immunological background to transplantation", J. Antimicrobial Chemotherapy, vol. 36, Supp.B, 1–9, 1995.

Ishizuka et al., "Low molecular weight immunomodulators produced by microorganisms", Int. J. of Immunopharmac., vol. 17, No. 2, 133–139, 1995.

Stevens et al., "Immunosuppressive agents in gastrointestinal disease", Current Opinion in Gastroenterology, vol. 11, 554–561, 1995.

*Primary Examiner*—Jose G. Dees
*Assistant Examiner*—Marina Lamm
*Attorney, Agent, or Firm*—Oblon, Spivak, McClelland, Maier & Neustadt, P.C.

[57] ABSTRACT

Described is a pyridine derivative represented by the following formula (1):

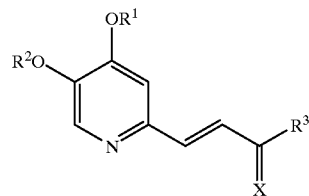

(1)

wherein $R^1$ and $R^2$ individually represent H, an alkyl group, a cycloalkyl group, a hydroxyalkyl group, an alkoxyalkyl group which may have a substituent, a carboxyalkyl group, an alkoxycarbonylalkyl group, an aralkyl group which may have a substituent, a phenacyl group or an acyl group, $R^3$ represents an alkyl group, a phenyl group which may have a substituent, a heteroaryl group or a cyclic amino group, X represents O or combination of OH and H, or a salt thereof; and a medicament, such as cytokine production suppressant, comprising the derivative or salt thereof as an effective ingredient. The invention compound has potential, highly specific and highly safe immunoregulating capacity so that it can suppress the excessive production of a specific cytokine in various diseases related to the immune system.

6 Claims, No Drawings

PYRIDINE DERIVATIVE AND MEDICAMENT CONTAINING THE SAME AS AN EFFECTIVE INGREDIENT

TECHNICAL FIELD

The present invention relates to a pyridine derivative. More specifically, this invention relates to a novel pyridine derivative or salt thereof having both excellent suppressive action against cytokine production and high safety; and a medicament comprising it as an effective ingredient.

BACKGROUND ART OF THE INVENTION

The immune system which is a defense mechanism of a living organism against exogenous or endogenous foreign bodies is formed of a marrow cell group typified by macrophages and neutrophils and a lymphocyte group such as T cells and B cells. These cell groups not only function independently but also act mutually through intercellular direct contact or soluble factors which are collectively called cytokine, thereby maintaining their homeostasis. The defense mechanism is so finely formed so that even the collapse of delicate balance induces a serious morbid state.

Such collapse of an immunocyte control mechanism triggers the production of autoantibodies or induces excessive immunoreaction, which is thought to cause collagen disease, systemic lupus erythematosus and various allergic diseases. It is known that in AIDS (acquired immunodeficiency syndrome), the infection of T cells with HIV causes decay of the immune system and this decay proceeds further. In addition, chronic diseases caused by diabetes or viruses or the development of a morbid state of a cancer also occurs partly because of the loss in immune balance.

In recent years, cytokine production suppressants such as cyclosporin and FK506, which have already been known as a rejection suppressant upon organ transplantation, have been used for the treatment of the above-described diseases. Besides, steroidal anti-inflammatory agents having inhibitory effects against cytokine production have been used for autoimmune diseases such as allergy, atopy and rheumatism and bronchial asthma and have achieved therapeutic effects to some extent.

It is well known that the immune system is indispensable for the temporary defense mechanism of a host and under the immunodeficient conditions induced by the administration of an immunosuppressant or a carcinostatic agent, the host is easily attacked by infectious diseases. At present, a medicament, for example, an immunosuppressant or steroidal anti-inflammatory agent, for suppressing the production of various cytokines cannot be applied freely to an autoimmune disease and it is limited in the administration method or drug holidays. For the treatment of the above diseases related to the immune system, there is accordingly a demand for the development of an immunoregulator with high specificity which acts on only a specific immune phenomenon.

An object of the present invention is therefore to provide a potential immunoregulator with high specificity and high safety which can suppress the excessive production of a specific cytokine in various immune diseases.

DISCLOSURE OF THE INVENTION

Under such situations, the present inventors have synthesized many compounds and studied their suppressive action against cytokine production. As a result, it has been found that a novel pyridine derivative represented by the below-described formula (1) or salt thereof strongly suppresses the production of interleukin (IL)-4 and IL-5, has high safety and has excellent immunoregulating action, leading to the completion of the present invention.

IL-4 and IL-5 are cytokines mainly produced by Th2 helper cells type 2 (Th2). IL-4 takes part in the differentiation of B cells and has a close relationship with the allergic reaction through IgE, while IL-5 takes part in the proliferation of B cells, production of IgA and activation of eosinophilic leukocyte. The compound according to the present invention strongly suppresses the production of IL-4 and IL-5 in the cytokine network so that exasperating or suppressing action on other cytokine production is expected.

The present invention provides a pyridine derivative represented by the following formula (1):

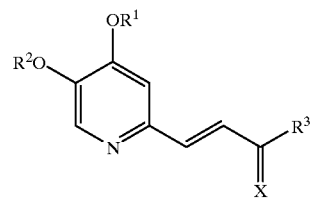

wherein $R^1$ and $R^2$ are the same or different and each independently represents a hydrogen atom, an alkyl group, a hydroxyalkyl group, an alkoxyalkyl group which may have a substituent, a carboxyalkyl group, an alkoxycarbonylalkyl group, an aralkyl group which may have a substituent, a phenacyl group or an acyl group, $R^3$ represents an alkyl group, a phenyl group which may have a substituent, a heteroaryl group or a cyclic amino group represented by the following formula (2):

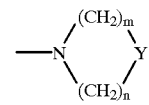

in which Y represents a methylene group or an oxygen atom, m stands for 1 to 2, n stands for an integer of 1 to 3, m+n stands for an integer of 3 to 5, X represents an oxygen atom or combination of a hydroxyl group and a hydrogen atom; or a salt thereof.

The present invention also provides a medicament comprising as an effective ingredient a pyridine derivative represented by the above formula (1) or salt thereof, more specifically, a cytokine production suppressant and immunoregulator.

The present invention further provides the use of a pyridine derivative represented by the above formula (1) or salt thereof as a medicament, more specifically, the use of it as a cytokine production suppressant and immunoregulator.

The present invention still further provides a therapeutic method for cytokine-production-induced diseases or immunodysfunction-induced diseases, which comprises administering to a patient an effective amount of a pyridine derivative represented by the above formula (1) or salt thereof.

BEST MODES FOR CARRYING OUT THE INVENTION

In the formula (1) representing a pyridine derivative of the present invention, examples of the alkyl group represented by $R^1$ or $R^2$ include linear, branched and cyclic alkyl groups. Exemplary linear or branched alkyl groups include $C_{1-8}$ alkyl groups such as methyl, ethyl, n-propyl, isopropyl, n-butyl, isobutyl, n-pentyl and n-hexyl; and exemplary cyclic alkyl groups include $C_{3-8}$ alkyl groups such as cyclopropyl, cyclobutyl, cyclopentyl, cyclohexyl and cycloheptyl. Illustrative hydroxyalkyl groups include $C_{1-8}$ ones such as hydroxymethyl, hydroxyethyl, hydroxypropyl, hydroxybutyl, hydroxypentyl, hydroxyhexyl and hydroxyheptyl groups. Examples of the alkoxyalkyl group which may have a substituent include $C_{1-8}$ alkoxy-$C_{1-8}$ alkyl groups which may be substituted by a $C_{1-8}$ alkoxyl, tri-$C_{1-8}$ alkylsilyl, phenyl or the like, such as methoxymethyl, methoxyethoxymethyl, 2-(trimethylsilyl)ethoxymethyl and benzyloxymethyl. Examples of the carboxyalkyl group include groups having a carboxyl group at one end of their linear $C_{1-8}$ alkylene chain. Examples of the alkoxycarbonylalkyl group include groups having an alkoxycarbonyl group at one end of their linear $C_{1-8}$ alkylene chain, the alkoxy group of said alkoxycarbonyl group being, for example, a $C_{1-8}$ alkoxyl group such as methoxyl, ethoxyl, n-propoxyl, isopropoxyl, n-butoxyl, isobutoxyl or t-butoxyl group). Examples of the aralkyl group which may have a substituent include a benzyl group, benzyl groups each having at the o-, m- or p-position at least one hydrogen atom, methoxycarbonyl group or methoxy group, and a phenetyl group. Examples of the acyl group include $C_{2-8}$ alkanoyl groups such as acetyl, propionyl, n-butyryl, isobutyryl, valeryl, isovaleryl and pivaloyl.

In the formula (1), examples of the alkyl group represented by $R^3$ include linear, branched and cyclic alkyl groups. Exemplary linear or branched alkyl groups include $C_{1-8}$ ones such as methyl, ethyl, n-propyl, isopropyl, n-butyl, isobutyl, n-pentyl and n-hexyl, while exemplary cyclic alkyl groups include $C_{3-8}$ ones such as cyclopropyl, cyclobutyl, cyclopentyl, cyclohexyl and cycloheptyl. Examples of the phenyl group which may have a substituent include phenyl groups which may have one or two substituents selected from halogen atoms, $C_{1-8}$ alkyl groups, $C_{1-8}$ alkoxyl groups, a cyano group and a nitro group. Specific examples include a phenyl group, 2-substituted phenyl groups such as 2-fluorophenyl, 2-chlorophenyl, 2-bromophenyl, 2-methylphenyl, 2-ethylphenyl, 2-isopropylphenyl, 2-tertbutylphenyl, 2-methoxyphenyl, 2-cyanophenyl and 2-nitrophenyl; 4-substituted phenyl groups such as 4-fluorophenyl, 4-chlorophenyl, 4-bromophenyl, 4-methylphenyl, 4-methoxyphenyl, 4-cyanophenyl and 4-nitrophenyl; and 2,6-disubstituted phenyl groups such as 2,6-difluorophenyl, 2,6-dichlorophenyl, 2,6-dibromophenyl and 2,6-dimethylphenyl. Examples of the heteroaryl group include furyl, thienyl, pyridyl, pyrimidyl and pyrazyl groups. Examples of the cyclic amino group represented by the above formula (2) include aziridino, azetidino, pyrrolidino, piperidino, hexahydroazepino and morpholino groups.

The pyridine derivative (1) or salt thereof according to the present invention may have optical isomers because it may contain an asymmetric carbon atom; or it may exist as solvated products such as hydrates. It is to be noted that these compounds are all embraced by the present invention.

The salt of the pyridine derivative (1) of the present invention is determined depending on the dissociated ions which differ with the base pyridine derivative (1). When the pyridine derivative (1) is basic, examples of the salt include hydrochloride, nitrate, hydrobromide, p-toluenesulfonate, methanesulfonate, fumarate, maleate, malonate, succinate, citrate and tartrate. When the pyridine derivative (1) is acidic, examples of the salt include sodium salt, potassium salt and ammonium salt.

The pyridine derivative (1) of the present invention is, for example, prepared based on the method in which a known compound (3) easily derived from kojic acid, which is available in a large amount and at a low cost, through two steps is introduced into a key intermediate (4), followed by Wittig reaction to obtain a pyridine derivative (1a) which is a part of the invention compound (1).

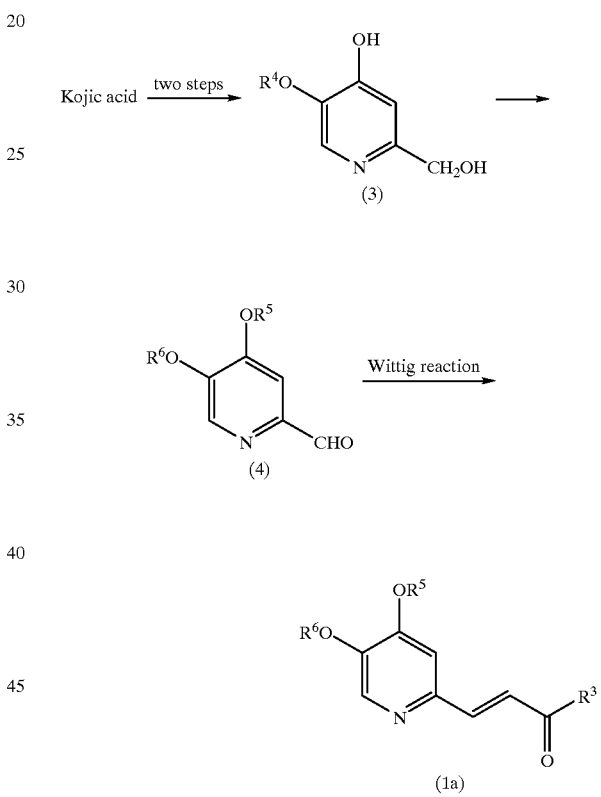

wherein $R^4$ represents an alkyl group, an alkoxyalkyl group which may have a substituent or an aralkyl group, $R^5$ and $R^6$ are the same or different and each independently represents an alkyl group, an alkoxyalkyl group which may have a substituent, an alkoxycarbonylalkyl group, an aralkyl group which may have a substituent, a phenacyl group or an acyl group and $R^3$ has the same meaning as defined above.

The key intermediate (4) can be obtained as Compound (4) or Compound (4a) which is a part of Compound (4) from the known Compound (3) in accordance with any one of the steps shown by the following reaction scheme.

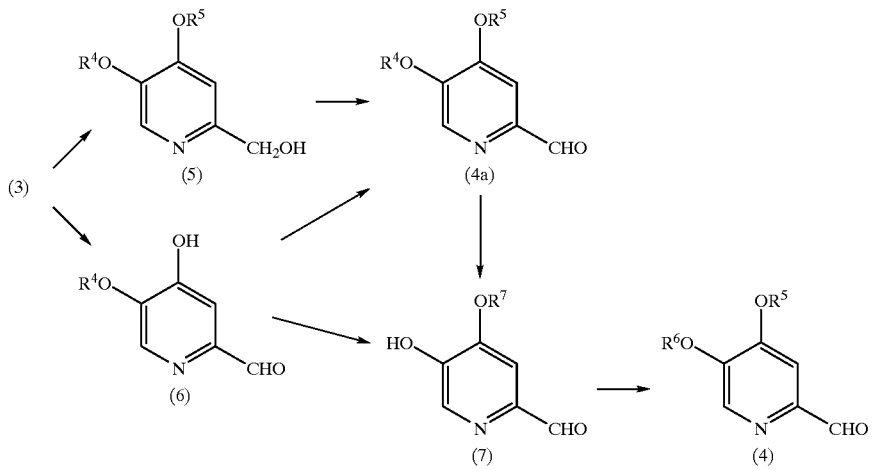

wherein $R^4$, $R^5$, and $R^6$ have the same meanings as defined above, and $R^7$ represents a hydrogen atom, an alkyl group, an alkoxyalkyl group which may have a substituent, an alkoxycarbonylalkyl group, an aralkyl group which may have a substituent or an acyl group.

Described specifically, Compound (4a) can be obtained by reacting Compound (3) with a halide reagent ($R^5$—Y in which Y represents a halogen atom) to convert it into Compound (5) and then reacting the resulting compound with an oxidizing agent; or by reacting Compound (3) with an oxidizing agent to convert it into Compound (6) and then reacting the resulting compound with a halide reagent or an acid anhydride ($R^{5a}$—O—$R^{5a}$ in which $R^{5a}$ represents an acyl group). Compound (4) can be obtained by deprotecting either Compound (4a) or Compound (6) wherein $R^4$ represents an alkoxyalkyl group which may have a substituent or a benzyl group which may have a substituent to convert it into Compound (7) and then reacting the resulting compound with a halide reagent or an acid anhydride. Incidentally, during the above reaction steps, an N-substituted compound is formed preferentially to an O-substituted compound upon reaction with a halide reagent, but it is possible to form the O-substituted compound preferentially by properly using substrates (3), (6) and (7) and a reaction reagent.

It is preferred that the reaction to obtain Compound (5) from Compound (3) by using a halide reagent is effected in a solvent such as alcohol, tetrahydrofuran, dimethylformamide or dimethylsulfoxide in the presence of a base such as potassium carbonate or sodium carbonate or, in some cases, potassium iodide or sodium iodide at a temperature ranging from room temperature to 80° C.; or in a water-alcohol mixed solvent in the presence of a base such as sodium hydroxide or potassium hydroxide at a temperature ranging from 0° C. to reflux temperature.

It is preferred that the reaction to obtain Compound (6) by the oxidation of Compound (3) is effected using as an oxidizing agent an excess amount of active manganese dioxide or barium manganate (VI) in a solvent such as tetrahydrofuran, 1,4-dioxane or dimethylformamide at a temperature ranging from room temperature to 100° C.

The reaction to obtain Compound (4a) by the oxidation of Compound (5) is effected easily by using as an oxidizing agent an excess amount of active manganese dioxide or barium manganate (VI) in a solvent such as chloroform, dichloromethane or acetone at a temperature ranging from room temperature to reflux temperature; by the oxidation (Parikh-Doering reaction) with a dimethylsulfoxide/sulfur trioxide-pyridine complex; or by the oxidation (Swern reaction) with dimethylsulfoxide/oxalyl chloride. Alternatively, Compound (4a) can also be obtained by utilizing the oxidation reaction with pyridinium chlorochromate (PCC) or pyridinium dichromate (PDC).

The reaction to obtain Compound (4a) from Compound (6) is effected by reacting Compound (6) with a halide reagent in the presence of a base such as sodium hydride or potassium hydride in a solvent such as tetrahydrofuran, 1,2-dimethoxyethane, dimethylformamide or dimethylsulfoxide at a temperature ranging from 0° C. to room temperature; or by reacting Compound (6) with a halide reagent in a solvent such as alcohol, tetrahydrofuran, dimethylformamide or dimethylsulfoxide in the presence of a base such as potassium carbonate or sodium carbonate or, in some cases, potassium iodide or sodium iodide at a temperature ranging from 0 to 80° C. When $R^5$ represents an acyl group, however, it is preferred to react with a halide reagent in a solvent such as dichloromethane or tetrahydrofuran in the presence of a tertiary amine such as triethylamine. When $R^5$ represents an acetyl group, it is most preferred to effect the reaction by the acetic anhydride/sodium acetate method at a temperature ranging from room temperature to 100° C.

In the reaction to obtain Compound (7) from Compound (4a) or Compound (6), employed is a compound having as $R^4$ an eliminative substituent such as a benzyl group which may have a substituent or an alkoxyalkyl group which may have a substituent. When $R^4$ represents a benzyl group which may have a substituent, a hydrogenation reaction in the presence of a palladium catalyst or Raney-nickel catalyst or a reductive elimination reaction with ammonium formate, cyclopentene or 1,4-cyclohexadiene is employed. When $R^4$ represents an alkoxyalkyl group which may have a substituent, on the other hand, the reaction to be employed differs with the kind of $R^4$. In the case of a methoxymethyl group, hydrogen chloride/isopropyl alcohol-tetrahydrofuran or dilute acetic acid is used; in the case of a methoxyethoxymethyl group, trifluoroacetic acid is used; and in the case of 2-(trimethylsilyl)ethoxymethyl group, sulfuric acid/methanoltetrahydrofuran or tetraalkylammonium fluoride is used, each for deprotection.

The reaction to obtain Compound (4) from Compound (7) is easily effected under the similar conditions to the reaction to obtain Compound (4a) from Compound (6).

The key intermediate (4) thus obtained and a Wittig reagent separately prepared are reacted by the Horner-Emmons reaction, whereby Compound (1a) can be obtained. This reaction is preferably effected in a solvent such as tetrahydrofuran, 1,2-dimethoxyethane, 1,4-dioxane or diethyl ether in the presence of a base such as sodium hydride or potassium hydride at a temperature ranging from 0° C. to the room temperature.

As an alternative method of the Wittig reaction, the key intermediate (4) or Compound (6) can be introduced into Compound (1a) or Compound (1d$_1$) by cross aldol condensation. This reaction is particularly effective when a compound having as $R^3$ a phenyl group which may have a substituent is used as the key intermediate.

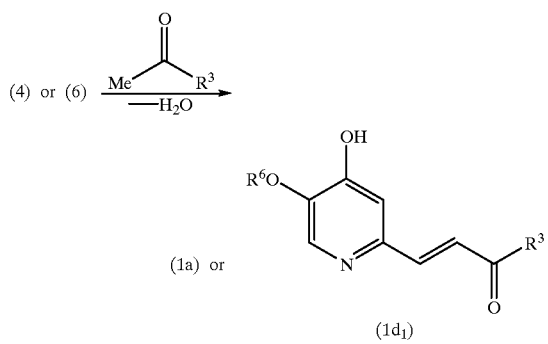

Wherein $R^3$ and $R^6$ have the same meanings as defined above.

The above reaction proceeds in the presence of various bases. It is easily effected in the presence of a base such as sodium hydroxide or potassium hydroxide in a mixed solvent of water and a lower alcohol at a temperature ranging from 0° C. to reflux temperature, or by using a catalytic amount of piperidine-acetic acid or piperidine-benzoic acid in a solvent such as benzene or toluene and distilling off water produced at the reflux temperature.

The hydrogen-substituted compound (1d$_1$) or (1d$_2$) can be introduced into the invention Compound (1a) by reacting the former with a halide reagent [$R^5$—Y or $R^6$—Y] or an acid anhydride [$R^{5a}$—O—$R^{5a}$ or $R^{6a}$—O—$R^{6a}$ in which $R^{5a}$ or $R^{6a}$ represents an acyl group] in the presence of a base.

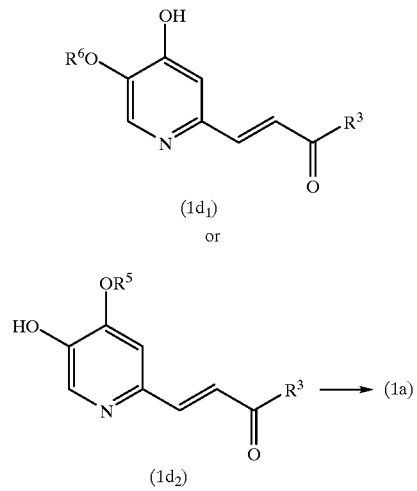

Wherein $R^3$, $R^5$ and $R^6$ have the same meanings as defined above.

The introduction of Compound (1d$_1$) or (1d$_2$) into Compound (1a) is effected by reacting Compound (1d$_1$) or (1d$_2$) with a halide reagent in the presence of a base such as sodium hydride or potassium hydride in a solvent such as tetrahydrofuran, 1,2-dimethoxyethane, dioxane, dimethylformamide or dimethylsulfoxide at a temperature ranging from 0° C. to room temperature; or by reacting Compound (1d$_1$) or (1d$_2$) with a halide reagent in the presence of a base such as potassium carbonate or sodium carbonate or, in some cases, potassium iodide or sodium iodide in a solvent such as alcohol, tetrahydrofuran, dimethylformamide or dimethylsulfoxide at a temperature ranging from room temperature to 80° C. In the case where $R^5$ or $R^6$ to be introduced represents an acyl group, however, it is preferred to react Compound (1d$_1$) or (1d$_2$) with a halide reagent in a solvent such as dichloromethane or tetrahydrofuran in the presence of a tertiary amine such as triethylamine. In the case where $R^5$ or $R^6$ to be introduced represents an acetyl group, it is most preferred to effect the above reaction by the acetic anhydride/sodium acetate method at a temperature ranging from room temperature to 100° C.

Next, the invention compound (1b) can be obtained by hydrolyzing the invention compound (1a$_1$) which has, among the invention compounds (1a), an alkoxycarbonylalkyl group as at least one of $R^5$ and $R^6$, an acyl group as at least one of $R^5$ and $R^6$, or an alkoxycarbonylalkyl group as one of $R^5$ and $R^6$ and an acyl group as another.

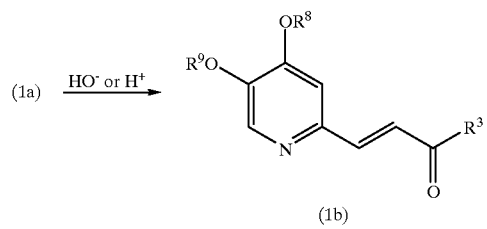

wherein $R^3$ has the same meaning as defined above, $R^8$ and $R^9$ are the same or different and each independently represents a hydrogen atom, an alkyl group, an alkoxyalkyl group which may have a substituent, a carboxyalkyl group or an aralkyl group which may have a substituent, with the proviso that at least one of $R^8$ and $R^9$ represents a hydrogen atom or a carboxyalkyl group.

The above hydrolysis reaction proceeds in either one of an alkali or acid. The invention compound (1b) can be obtained in a high yield by the most generally employed method, that is, by carrying out the hydrolysis with a dilute aqueous solution of sodium hydroxide or potassium hydroxide in a lower alcohol at a temperature ranging from room temperature to the reflux temperature.

The invention compound (1a) or (1b) can be introduced into the invention compound (1c) (the compound represented by the formula (1) in which X represents the combination of a hydroxyl group and a hydrogen atom), which is an alcohol, by reducing the carbonyl group of the α,β-unsaturated ketone portion of the invention compound (1a) or (1b).

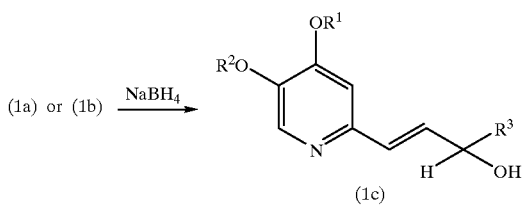

wherein $R^1$, $R^2$ and $R^3$ have the same meanings as defined above.

The above reaction is effected, in the presence of sodium borohydride or its related reagent (such as sodium trimethoxyborohydride, sodium cyanoborohydride or sodium triacetoxyborohydride) which is inert to a carboxylic acid or derivative thereof, in a solvent such as methanol, ethanol, isopropyl alcohol, dimethylsulfoxide or acetic acid at a temperature ranging from −20° C. to room temperature.

Next, the invention compound (1e) can be obtained by hydrolyzing the invention compound ($1c_1$), among the invention compounds (1c), which has an alkoxycarbonylalkyl group as at least one of $R^1$ and $R^2$, an acyl group as at least one of $R^1$ and $R^2$, or an alkoxycarbonylalkyl group as one of $R^1$ and $R^2$ and an acyl group as another.

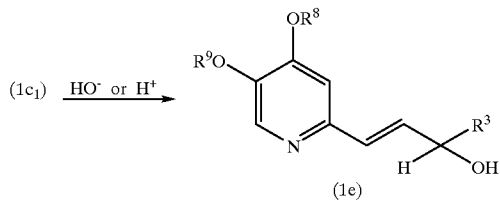

wherein $R^3$, $R^8$ and $R^9$ have the same meanings as defined above.

The above hydrolysis reaction proceeds in either one of an alkali or acid. The invention compound (1e) can be obtained in a high yield by the most usually employed method, that is, by carrying out the hydrolysis with a dilute aqueous solution of sodium hydroxide or potassium hydroxide in a lower alcohol at a temperature ranging from room temperature to the reflux temperature.

Alternatively, a known compound (8) can be introduced into the invention compound (1f) by the dehydration condensation reaction with a cyclic amine.

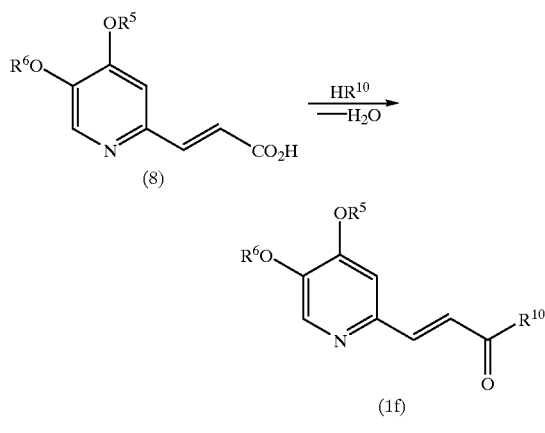

wherein $R^{10}$ represents a group:

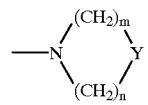

in which Y represents a methylene group or an oxygen atom, m stands for 1 to 2, n stands for an integer of 1 to 3, m+n represents an integer of 3 to 5, and $R^5$ and $R^6$ have the same meanings as defined above.

The above reaction is effected readily by using as a base a tertiary amine at a temperature ranging from 0° C. to room temperature in the presence of a condensation agent such as dicyclohexylcarbodiimide (DCC) in a solvent such as dichloromethane or chloroform, or in the presence of a condensation agent such as diphenylphosphorylcyanide in a solvent such as tetrahydrofuran, 1,2-dimethoxyethane, dioxane, dimethylformamide or dimethylsulfoxide.

In the above reaction, the invention compound (1) can be isolated from the final reaction mixture in a manner known per se in the art, for example, solvent extraction, recrystallization or column chromatography.

The invention compound (1) can be formed into immunoregulators of various forms such as tablets, granules, powders, capsules, suspensions, injections, suppositories or external preparations. Described specifically, in the case of a solid preparation, it is preferred to add to the invention compound (1) an excipient and optionally a binder, a disintegrator, an extender, a coating agent and/or sugar coating agent; and then form the resulting mixture into tablets, granules, capsules, suppositories or the like in a manner known per se in the art. The invention compound (1) can be formed as an injection in the liquid form by dissolving, dispersing or emulsifying it in advance in a water carrier such as distilled water for injection; or as injection powders to be reconstituted with a diluent immediately before use. The injection is administered intravenously, arterially, intraperitoneally or subcutaneously or by drip infusion.

When a medicament according to the present invention is administered to a patient, examples of the disease include cytokine-production-induced diseases and immunodysfunction-induced diseases. Specific examples include rejection reaction upon organ transplantation, autoimmune diseases such as allergy, atopy and rheumatism, bronchial asthma, IgA glomerulonephritis, osteoporosis, inflammation, cancers and HIV infection.

In the above diseases, the dosage of the medicament of the present invention differs with the administration route or symptoms, age or sex of the patient. When orally administered, the medicament is preferably administered at a dose of 0.001 to 10 mg/kg, particularly 0.01 to 1 mg/kg in terms of the pyridine derivative (1) or salt thereof per adult once or in several portions a day.

EXAMPLES

The present invention will hereinafter be described by examples and referential examples. It should however be borne in mind that the present invention is not limited to or by these examples. Incidentally, in the following examples, "Me" means a methyl group, "Et" an ethyl group, "Ph" a phenyl group, "Bn" a benzyl group and "Ac" an acetyl group.

Example 1

Synthesis of 4,5-dimethoxy-2-(3-oxo-3-phenyl-1-propenyl)pyridine [in the formula (1), $R^1=R^2$=Me, $R^3$=Ph, X=O]

In 35 ml of tetrahydrofuran, 0.60 g (14.9 mmol) of 60% sodium hydride was suspended, followed by the dropwise addition of 3.83 g (14.9 mmol) of diethyl (2-oxo-2-phenylethyl)phosphonate while stirring at 0° C. under a nitrogen atmosphere. Ten minutes later, a 5 ml tetrahydrofuran solution containing 2.27 g (13.6 mmol) of 4,5-dimethoxypyridin-2-aldehyde was added dropwise to the reaction mixture and the resulting mixture was stirred for 3 hours under the same conditions. The reaction mixture was poured into an ice-cooled 5% aqueous solution of ammonium chloride, followed by extraction with ethyl acetate. The organic layer was washed with saturated saline, dried and then concentrated under reduced pressure. The crystals so precipitated were recrystallized from acetone-isopropyl ether, whereby 3.04 g (yield: 83%) of the title compound were obtained.

Melting point: 115–116° C.; $^1$H-NMR δ ppm(CDCl$_3$): 3.90(3H,s), 4.00(3H,s), 7.01(1H,s), 7.40–7.80(3H,m), 7.81(1H,d), 7.93(1H,d), 8.00–8.20(2H,m), 8.28(1H,s).

Example 2

In a similar manner to Example 1, the following compound was obtained.
4-Cyclopentyloxy-5-methoxy-2-(3-oxo-3-phenyl-1-propenyl)pyridine [in the formula (1), $R^1$=cyclopentyl, $R^2$=Me, $R^3$=Ph, X=O}

Melting point: 113–114° C.; $^1$H-NMR δ ppm(CDCl$_3$): 1.64–2.05(8H,m), 3.97(3H,s), 4.86–4.89(1H,m), 7.00(1H,s), 7.48–7.52(2H,m), 7.56–7.59(1H,m), 7.70(1H,d), 7.94(1H,d), 8.07–8.09(2H,m), 8.21(1H,s).

Example 3

In a similar manner to Example 1, the following compound was obtained.
4-Benzyloxy-5-methoxy-2-(3-oxo-3-phenyl-1-propenyl)pyridine [in the formula (1), $R^1$=Bn, $R^2$=Me, $R^3$=Ph, X=O}

Melting point: 104–105° C.; $^1$H-NMR δ ppm(CDCl$_3$): 4.01(3H,s), 5.24(2H,s), 7.04(1H,s), 7.35–7.51(7H,m), 7.56–7.60(1H,m), 7.65(1H,d), 7.90(1H,d), 8.05–8.07(2H,m), 8.24(1H,s).

Example 4

In a similar manner to Example 1, the following compound was obtained.
5-Methoxy-4-methoxymethyloxy-2-(3-oxo-3-phenyl-1-propenyl)pyridine [in the formula (1), $R^1$=—CH$_2$OMe, $R^2$=Me, $R^3$=Ph, X=O]

Melting point: 99–100° C.; $^1$H-NMR δ ppm(CDCl$_3$): 3.54(3H,s), 4.02(3H,s), 5.36(2H,s), 7.36(1H,s), 7.42–7.64(3H,m), 7.70(1H,d), 7.95(1H,d), 8.00–8.18(2H,m), 8.32(1H,s).

Example 5

In a similar manner to Example 1, the following compound was obtained.
4,5-Bis(methoxymethyloxy)-2-(3-oxo-3-phenyl-1-propenyl)pyridine [in the formula (1), $R^1=R^2$=—CH$_2$OMe, $R^3$=Ph, X=O]

Melting point: 67–68° C.; $^1$H-NMR δ ppm(CDCl$_3$): 3.53(3H,s), 3.56(3H,s), 5.31(2H,s), 5.36(2H,s), 7.35(1H,s), 7.48–7.66(3H,m), 7.70(1H,d), 8.00(1H,d), 8.00–8.20(2H,m), 8.53(1H,s).

Example 6

In a similar manner to Example 1, the following compound was obtained.
5-Acetoxy-4-methoxy-2-(3-oxo-3-phenyl-1-propenyl)pyridine [in the formula (1), $R^1$=Me, $R^2$=Ac, $R^3$=Ph, X=O]

Melting point: 131–132° C.; $^1$H-NMR δ ppm(CDCl$_3$): 2.35(3H,s), 3.94(3H,s), 7.11(1H,s), 7.48–7.66(3H,m), 7.72(1H,d), 8.10(1H,d), 8.02–8.20(2H,m), 8.32(1H,s).

Example 7

In a similar manner to Example 1, the following compound was obtained.
4-Acetoxy-5-methoxy-2-(3-oxo-3-phenyl-1-propenyl)pyridine [in the formula (1), $R^1$=Ac, $R^2$=Me, $R^3$=Ph, X=O}

Melting point: 137–138° C.; $^1$H-NMR δ ppm(CDCl$_3$): 2.36(3H,s), 4.00(3H,s), 7.30(1H,s), 7.40–7.66(3H,m), 7.70(1H,d), 7.97(1H,d), 8.00–8.18(2H,m), 8.46(1H,s).

Example 8

In a similar manner to Example 1, the following compound was obtained.
4,5-Diacetoxy-2-(3-oxo-3-phenyl-1-propenyl)pyridine [in the formula (1), $R^1=R^2$=Ac, $R^3$=Ph, X=O}

Melting point: 148–149° C.; $^1$H-NMR δ ppm(CDCl$_3$): 2.34(3H,s), 2.35(3H,s), 7.42(1H,s), 7.49–7.53(2H,m), 7.58–7.62(1H,m), 7.71(1H,d), 8.06(1H,d), 8.07–8.09(2H,m), 8.54(1H,s).

Example 9

In a similar manner to Example 1, the following compound was obtained.
4-Cyclopentyloxy-5-methoxy-2-(3-oxo-1-octenyl)pyridine [in the formula (1), $R^1$=cyclopentyl, $R^2$=Me, $R^3$=—(CH$_2$)$_4$CH$_3$, X=O]

Melting point: 37–38° C.; $^1$H-NMR δ ppm(CDCl$_3$): 0.88–0.92(3H,m), 1.32–1.34(4H,m), 1.66–2.04(10H,m), 2.65–2.69(2H,m), 3.95(3H,s), 4.84–4.87(1H,m), 6.97–7.01(2H,m), 7.48(1H,d), 8.16(1H,s).

Example 10

In a similar manner to Example 1, the following compound was obtained.
2-(3-Cyclopentyl-3-oxo-1-propenyl)-4-cyclopentyloxy-5-methoxypyridine [in the formula (1), $R^1=R^3$=cyclopentyl, $R^2$=Me, X=O]

Melting point: 56–57° C.; $^1$H-NMR δ ppm(CDCl$_3$): 1.59–2.04(16H,m), 3.20–3.25(1H,m), 3.95(3H,s), 4.83–4.88(1H,m), 6.98(1H,s), 7.07(1H,d), 7.50(1H,d), 8.16(1H,s).

Example 11

In a similar manner to Example 1, the following compound was obtained.
4,5-diacetoxy-2-(3-oxo-1-octenyl)pyridine [in the formula (1), $R^1=R^2$=Ac, $R^3$=—(CH$_2$)$_4$CH$_3$, X=O]

Melting point: 59–60° C.; $^1$H-NMR δ ppm(CDCl$_3$): 0.91(3H,t), 1.30–1.37(4H,m), 1.65–1.72(2H,m), 2.67(2H,t), 2.33(3H,s), 2.35(3H,s), 7.14(1H,d), 7.40(1H,s), 7.49(1H,d), 8.50(1H,s).

Example 12

In a similar manner to Example 1, the following compound was obtained as a pale yellow oil.
Ethyl 6-[5-methoxy-2-(3-oxo-3-phenyl-1-propenyl)-4-pyridyloxy]hexanoate [in the formula (1), $R^1$=—$(CH_2)_5CO_2Et$, $R^2$=Me, $R^3$=Ph, X=O]

$^1$H-NMR δ ppm(CDCl$_3$): 1.26(3H,t), 1.51–1.57(2H,m), 1.69–1.76(3H,m), 1.88–1.95(2H,m), 2.33–2.37(2H,m), 3.99 (3H,s), 4.09–4.16(3H,m), 7.01(1H,s), 7.48–7.52(2H,m), 7.56–7.60(1H,m), 7.70(1H,d), 7.93(1H,d), 8.07–8.09(2H, m), 8.22(1H,s).

Example 13

In a similar manner to Example 1, the following compound was obtained.
Ethyl 4-[5-methoxy-2-(3-oxo-1-octenyl)-4-pyridyloxy]butanoate [in the formula (1), $R^1$=—$(CH_2)_3CO_2Et$, $R^2$=Me, $R^3$=—$(CH_2)_4CH_3$, X=O]

Melting point: 59–60° C.; $^1$H-NMR δ ppm(CDCl$_3$): 0.90 (3H,t), 1.27(3H,t), 1.31–1.35(4H,m), 1.65–1.72(2H,m), 2.16–2.23(2H,m), 2.54(2H,t), 2.67(2H,t), 3.97(3H,s), 4.13 (2H,t), 4.16(2H,q), 7.00(1H,d), 7.05(1H,s), 7.48(1H,d), 8.18 (1H,s).

Example 14

In a similar manner to Example 1, the following compound was obtained.
Ethyl 6-[5-benzyloxy-2-(3-oxo-1-octenyl)-4-pyridyloxy] hexanoate [in the formula (1), $R^1$=—$(CH_2)_5CO_2Et$ $R^2$=Bn, $R^3$=—$(CH_2)_4CH_3$, X=O]

Melting point: 76–77° C.; $^1$H-NMR δ ppm(CDCl$_3$): 0.90 (3H,t), 1.25(3H,t), 1.27–1.34(4H,m), 1.52–1.75(6H,m), 1.88–1.92(2H,m), 2.34(2H,t), 2.66(2H,t), 4.10(2H,t), 4.13 (2H,q), 5.22(2H,s), 7.00(1H,d), 7.00(1H,s), 7.32–7.42(5H, m), 7.46(1H,d), 8.18(1H,s).

Example 15

In a similar manner to Example 1, the following compound was obtained.
Methyl 6-[5-methoxy-2-(3-oxo-1-octenyl)-4-pyridyloxy] hexanoate [in the formula (1), $R^1$=—$(CH_2)_5CO_2Me$, $R^2$=Me, $R^3$=—$(CH_2)_4CH_3$, X=O]

Melting point: 57–58° C.; $^1$H-NMR δ ppm(CDCl$_3$):
0.88–0.92(3H,m), 1.24–1.76(10H,m), 1.86–1.92(2H,m), 2.36(2H,t), 2.67(2H,t), 3.67(3H,s), 3.97(3H,s), 4.06–4.14 (2H,m), 6.98(1H,d), 6.99(1H,s), 7.48(1H,d), 8.17(1H,s).

Example 16

In a similar manner to Example 1, the following compound was obtained.
Methyl 4-[5-methoxy-2-(3-oxo-3-phenyl-1-propenyl)-4-pyridyloxy]butanoate [in the formula (1), $R^1$=—$(CH_2)_3CO_2Me$, $R^2$=Me, $R^3$=Ph, X=O]

Melting point: 108–109° C.; $^1$H-NMR δ ppm(CDCl$_3$): 2.18–2.24(2H,m), 2.54–2.58(2H,m), 3.71(3H,s), 3.98(3H,s), 4.16–4.19(2H,m), 7.09(1H,s), 7.48–7.52(2H,m), 7.56–7.60 (1H,m), 7.71(1H,d), 7.94(1H,d), 8.03–8.10(2H,m), 8.22(1H, s).

Example 17

In a similar manner to Example 1, the following compound was obtained.
Methyl 6-[4-methoxy-2-(3-cyclopentyl-3-oxo-1-propenyl)-5-pyridyloxy]hexanoate [in the formula (1), $R^1$=Me, $R^2$=—$(CH_2)_5CO_2Me$, $R^3$=cyclopentyl, X=O]

Melting point: 69–70° C.; $^1$H-NMR δ ppm(CDCl$_3$): 1.50–1.75(8H,m), 1.84–1.91(6H,m), 2.33–2.37(2H,m), 3.19–3.23(1H,m), 3.67(3H,s), 3.93(3H,s), 4.10–4.14(2H,m), 7.00(1H,s), 7.08(1H,d), 7.51(1H,d), 8.16(1H,s).

Example 18

In a similar manner to Example 1, the following compound was obtained.
Methyl 4-[4-methoxy-2-(3-cyclopentyl-3-oxo-1-propenyl)-5-pyridyloxy]butanoate [in the formula (1), $R^1$=Me, $R^2$=$(CH_2)_3CO_2Me$, $R^3$=cyclopentyl, X=O]

Melting point: 113–114° C.; $^1$H-NMR δ ppm(CDCl$_3$): 1.60–1.72(4H,m), 1.84–1.91(4H,m), 2.14–2.21(2H,m), 2.54–2.58(2H,m), 3.19–3.23(1H,m), 3.69(3H,s), 3.93(3H,s), 4.15–4.18(2H,m), 7.00(1H,s), 7.08(1H,d), 7.50(1H,d), 8.17 (1H,s).

Example 19

Synthesis of 4-hydroxy-5-methoxy-2-(3-oxo-3-phenyl-1-propenyl)-pyridine [in the formula (1), $R^1$=H, $R^2$=Me, $R^3$=Ph, X=O]

To 1.50 g (5 mmol) of 5-methoxy-4-methoxymethyloxy-2(3-oxo-3-phenyl-1-propenyl)pyridine [in the formula (1), $R^1$=—$CH_2OMe$, $R^2$=Me, $R^3$=Ph, X=O] which had been obtained in Example 4, 20 ml of trifluoroacetic acid were added. The resulting mixture was stirred at room temperature for 30 minutes, followed by concentration under reduced pressure. Chloroform was added to the residue and the crystals so precipitated were collected by filtration. The crystals so obtained were added to 30 ml of a saturated aqueous solution of sodium bicarbonate and they were stirred at room temperature for 5 hours. After collection by filtration, the crystals were recrystallized from ethanol-acetone, whereby 1.22 g (yield: 96%) of the title compound were obtained.

Melting point: 197–198° C.; $^1$H-NMR δ ppm(DMSO-d$_6$): 3.87(3H,s), 7.14(1H,s), 7.54(1H,d), 7.55–7.61(2H,m), 7.65–7.70(1H,m), 7.93(1H,d), 8.02(1H,s), 8.06–8.10(2H, m), 10.75(1H,br).

Example 20

In a similar manner to Example 19, the following compound was obtained.
4,5-Dihydroxy-2-(3-oxo-3-phenyl-1-propenyl)pyridine [in the formula (1), $R^1$=$R^2$=H, $R^3$=Ph, X=O]

Melting point: 135–137° C.; $^1$H-NMR δ ppm(DMSO-d$_6$): 4.40(2H,br), 7.06(1H,s), 7.51(1H,d), 7.55–7.62(2H,m), 7.65–7.72(1H,m), 7.80(1H,br), 7.92(1H,d), 8.06–8.10(2H, m).

Example 21

Synthesis of 5-hydroxy-4-methoxy-2-(3-oxo-3-phenyl-1-propenyl)pyridine [in the formula (1), $R^1$=Me, $R^2$=H, $R^3$=Ph, X=O]

In 20 ml of methanol, were suspended 1.19 g (4 mmol) of 5-acetoxy-4-methoxy-2-(3-oxo-3-phenyl-1-propenyl) pyridine [in the formula (1), $R^1$=Me, $R^2$=Ac, $R^3$=Ph, X=O] which had been obtained in Example 6. To the resulting suspension, 1.10 g (8 mmol) of potassium carbonate were added, followed by stirring at room temperature for one hour. The reaction mixture was ice-cooled, followed by the addition of 10% hydrochloric acid. The crystals so precipitated were collected by filtration and washed with water. The crystals were recrystallized from ethyl acetate, whereby 0.77 g (yield: 75%) of the title compound was obtained.

Melting point: 161–163° C.; $^1$H-NMR δ ppm(CDCl$_3$): 3.97(3H,s), 5.22(1H,br), 7.07(1H,s), 7.42–7.66(3H,m), 7.70 (1H,d), 8.00(1H,d), 8.02–8.18(2H,m), 8.32(1H,s)

Example 22

In a similar manner to Example 21, the following compound was obtained.
4,5-Dihydroxy-2-(3-oxo-1-octenyl)pyridine [in the formula (1), $R^1=R^2=H$, $R^3=-(CH_2)_4CH_3$, $X=O$]

Melting point: 227–229° C.; $^1$H-NMR δ ppm(DMSO-$d_6$): 0.87(3H,t), 1.23–1.33(4H,m), 1.52–1.59(2H,m), 2.65(2H,t), 6.88(1H,bs), 6.89(1H,d), 7.35(1H,d), 7.76(1H,bs)

Example 23

Synthesis of 4,5-dimethoxy-2-(3-hydroxy-3-phenyl-1-propenyl)pyridine [in the formula (1), $R^1=R^2=Me$, $R^3=Ph$, X=combination of OH and H]

In 50 ml of methanol, were dissolved 1.35 g (5 mmol) of 4,5-dimethoxy-2-(3-oxo-3-phenyl-1-propenyl)pyridine [in the formula (1), $R^1=R^2=Me$, $R^3=Ph$, $X=O$] which had been obtained in Example 1. To the resulting solution, 0.76 g (20 mmol) of sodium borohydride was added, followed by stirring at 0° C. for 4 hours. The reaction mixture was poured into 150 ml of an ice-cooled 5% aqueous solution of ammonium chloride. The resulting mixture was extracted with dichloromethane. The organic layer was washed with saturated saline, dried and then concentrated under reduced pressure. The crystals so precipitated were recrystallized from acetone-isopropyl ether, whereby 1.12 g (yield: 83%) of the title compound were obtained.

Melting point: 145–146° C.; $^1$H-NMR δ ppm(CDCl$_3$): 3.4(1H,br), 3.89(3H,s), 3.90(3H,s), 5.42(1H,d), 6.67(1H, dd), 6.75(1H,d), 6.86(1H,s), 7.28–7.31(1H,m), 7.34–7.38 (2H,m), 7.44–7.46(2H,m), 7.97(1H,s)

Example 24

In a similar manner to Example 23, the following compound was obtained.
4-Hydroxy-2-(3-hydroxy-3-phenyl-1-propenyl)-5-methoxypyridine [in the formula (1), $R^1=H$, $R^2=Me$, $R^3=Ph$, X=combination of OH and H]

Melting point: 198–200° C.; $^1$H-NMR δ ppm(DMSO-$d_6$): 3.4(1H,br), 3.71(3H,s), 5.26(1H,d), 5.7(1H,br), 6.43(1H,s), 6.46(1H,s), 6.59(1H,dd), 7.23–7.26(1H,m), 7.32–7.39(4H, m), 7.49(1H,s)

Example 25

In a similar manner to Example 23, the following compound was obtained.
4,5-Dihydroxy-2-(3-hydroxy-3-phenyl-1-propenyl)pyridine [in the formula (1), $R^1=R^2=H$, $R^3=Ph$, X=combination of OH and H]

Melting point: 113–115° C.; $^1$H-NMR δ ppm(DMSO-$d_6$): 5.24(1H,d), 6.37–6.80(2H,m), 6.63(1H,s), 6.8(3H,br), 7.22–7.37(5H,m), 7.49(1H,s)

Example 26

In a similar manner to Example 23, the following compound was obtained.
Methyl 6-[2-(3-hydroxy-3-phenyl-1-propenyl)-5-methoxy-4-pyridyloxy]hexanoate [in the formula (1), $R^1=-(CH_2)_5CO_2Me$, $R^2=Me$, $R^3=Ph$, X=combination of OH and H]

Melting point: 94–95° C.; $^1$H-NMR δ ppm(CDCl$_3$): 1.47–1.53(2H,m), 1.66–1.72(2H,m), 1.83–1.88(2H,m), 2.32–2.36(2H,m), 3.66(3H,s), 3.88(3H,s), 4.01–4.04(2H,m), 5.41(1H,d), 6.64(1H,dd), 6.72(1H,d), 6.83(1H,s), 7.28–7.37 (3H,m), 7.43–7.45(2H,m), 7.99(1H,s)

Example 27

In a similar manner to Example 23, the following compound was obtained.
Ethyl 6-[2-(3-hydroxy-3-phenyl-1-propenyl)-5-methoxy-4-pyridyloxy]hexanoate [in the formula (1), $R^1=-(CH_2)_5CO_2Et$, $R^2=Me$, $R^3=Ph$, X=combination of OH and H]

Melting point: 97–98° C.; $^1$H-NMR δ ppm(CDCl$_3$): 1.25 (3H,t), 1.47–1.53(2H,m), 1.66–1.73(2H,m), 1.83–1.90(2H, m), 2.31–2.34(2H,m), 2.94(1H,bs), 3.89(3H,s), 4.01–4.05 (2H,m), 4.12(2H,q), 5.41(1H,d), 6.66(1H,dd), 6.72(1H,d), 6.83(1H,s), 7.26–7.37(3H,m), 7.43–7.45(2H,m), 8.00(1H,s)

Example 28

In a similar manner to Example 23, the following compound was obtained as a colorless oil.
Methyl 4-[2-(3-hydroxy-3-phenyl-1-propenyl)-4-methoxy-5-pyridyloxy]butanoate [in the formula (1), $R^1=Me$, $R^2=-(CH_2)_3CO_2Me$, $R^3=Ph$, X=combination of OH and H]

$^1$H-NMR δ ppm(CDCl$_3$): 2.10–2.17(2H,m), 2.54(2H,t), 3.68(3H,s), 3.87(3H,s), 4.05–4.14(3H,m), 5.42(1H,d), 6.67 (1H,dd), 6.73(1H,d), 6.85(1H,s), 7.27–7.30(1H,m), 7.34–7.38(2H,m), 7.43–7.45(2H,m), 8.01(1H,s)

Example 29

In a similar manner to Example 23, the following compound was obtained.
Methyl 4-[2-(3-hydroxy-3-phenyl-1-propenyl)-5-methoxy-4-pyridyloxy]butanoate [in the formula (1), $R^1=-(CH_2)_3CO_2Me$, $R^2=Me$, $R^3=Ph$, X=combination of OH and H]

Melting point: 106–107° C.; $^1$H-NMR δ ppm(CDCl$_3$): 2.13–2.20(2H,m), 2.51–2.55(2H,m), 3.68(3H,s), 3.88(3H,s), 4.07–4.10(2H,m), 5.41(1H,d), 6.65(1H,dd), 6.72(1H,d), 6.87(1H,s), 7.28–7.30(1H,m), 7.34–7.37(2H,m), 7.43–7.45 (2H,m), 8.00(1H,s)

Example 30

In a similar manner to Example 23, the following compound was obtained as a colorless oil.
Methyl 6-[2-(3-hydroxy-1-octenyl)-5-methoxy-4-pyridyloxy]hexanoate [in the formula (1), $R^1=-(CH_2)_5CO_2Me$, $R^2=Me$, $R^3=-(CH_2)_4CH_3$, X=combination of OH and H]

$^1$H-NMR δ ppm(CDCl$_3$): 0.87–0.92(3H,m), 1.23–1.75 (14H,m), 1.85–2.33(2H,m), 2.33–2.37(2H,m), 3.67(3H,s), 3.91(3H,s), 4.04–4.15(2H,m), 6.52(1H,dd), 6.59(1H,d), 6.82(1H,s), 8.06(1H,s)

Example 31

In a similar manner to Example 23, the following compound was obtained as a colorless oil.
Methyl 6-[2-(3-cyclopentyl-3-hydroxy-1-propenyl)-4-methoxy5-pyridyloxy]hexanoate [in the formula (1), $R^1=Me$, $R^2=-(CH_2)_5CO_2Me$, $R^3=$cyclopentyl, X=combination of OH and H]

$^1$H-NMR δ ppm(CDCl$_3$): 1.33–1.88(14H,m), 2.04–2.10 (2H,m), 2.33–2.37(2H,m), 3.67(3H,s), 3.91(3H,s), 4.04–4.08(2H,m), 4.11(1H,dd), 6.55(1H,dd), 6.60(1H,d), 6.83(1H,s), 8.05(1H,s)

Example 32

In a similar manner to Example 23, the following compound was obtained as a colorless oil.
Methyl 4-[2-(3-cyclopentyl-3-hydroxy-1-propenyl)-4-methoxy-5-pyridyloxy]butanoate [in the formula (1), $R^1$=Me, $R^2$=—$(CH_2)_3CO_2$Me, $R^3$=cyclopentyl, X=combination of OH and H]

$^1$H-NMR δ ppm(CDCl$_3$): 1.25–1.85(10H,m), 2.04–2.18 (2H,m), 2.53–2.57(2H,m), 3.69(3H,s), 3.90(3H,s), 4.09–4.15(3H,m), 6.56(1H,dd), 6.61(1H,d), 6.83(1H,s), 8.06(1H,s)

Example 33

Synthesis of 4-[5-methoxy-2-(3-oxo-3-phenyl-1-propenyl)-4-pyridyloxy]butanoic acid [in the formula (1), $R^1$=—$(CH_2)_3CO_2$H, $R^2$=Me, $R^3$=Ph, X=O]

In 16 ml of methanol was dissolved 0.71 g (2 mmol) of methyl 4-[5-methoxy-2-(3-oxo-3-phenyl-1-propenyl)-4-pyridyloxy]butanoate [in the formula (1), $R^1$=—$(CH_2)_3CO_2$Me, $R^2$=Me, $R^3$=Ph, X=O] which had been obtained in Example 16. To the resulting solution, 4 ml of a 1N aqueous solution of sodium hydroxide were added, followed by stirring at room temperature for 4 hours. To the reaction mixture, 4 ml of 1N hydrochloric acid were added. The resulting mixture was concentrated under reduced pressure as soon as possible. The residue was extracted with hot ethanol and recrystallized from ethanol, whereby 0.54 g (yield: 79%) of the title compound was obtained.

Melting point: 167–169° C.; $^1$H-NMR δ ppm(DMSO-d$_6$): 1.95–2.08(2H,m), 2.41(2H,t), 3.92(3H,s), 4.18(2H,t), 7.56–7.71(5H,m), 7.98(1H,d), 8.06–8.10(2H,m), 8.29(1H, s), 12.2(1H,br)

Example 34

In a similar manner to Example 33, the following compound was obtained.

4-[2-(3-Hydroxy-3-phenyl-1-propenyl)-5-methoxy-4-pyridyloxy]butanoic acid [in the formula (1), $R^1$=—$(CH_2)_3CO_2$H, $R^2$=Me, $R^3$=Ph, X=combination of OH and H]

Melting point: 165–166° C.; $^1$H-NMR δ ppm(DMSO-d$_6$): 1.91–1.98(2H,m), 2.35–2.50(2H,m), 3.82(3H,s), 4.04–4.09 (2H,m), 5.24–5.27(1H,m), 5.55–5.56(1H,m), 6.57 (1H,d), 6.67(1H,dd), 7.11(1H,s), 7.21–7.25(1H,m), 7.30–7.34(2H, m), 7.35–7.40(2H,m), 8.01(1H,s), 8.06(1H,bs)

Example 35

In a similar manner to Example 33, the following compound was obtained.

6-[2-(3-Hydroxy-1-octenyl)-5-methoxy-4-pyridyloxy] hexanoic acid [in the formula (1), $R^1$=—$(CH_2)_5CO_2$H, $R^2$=Me, $R^3$=—$(CH_2)_4CH_3$, X=combination of OH and H]

Melting point: 115–117° C.; $^1$H-NMR δ ppm(DMSO-d$_6$): 0.84–0.87(3H,m), 1.25–1.57(12H,m), 1.69–1.74(2H,m), 2.08–2.15(2H,m), 3.82(3H,s), 3.78–4.12(5H,m), 6.46(1H, d), 6.55(1H,dd), 7.06(1H,s), 8.06(1H,s)

Example 36

In a similar manner to Example 33, the following compound was obtained.

6-[2-(3-Cyclopentyl-3-hydroxy-1-propenyl)-4-methoxy-5-pyridyloxy]hexanoic acid hydrochloride [in the formula (1), $R^1$=Me, $R^2$=—$(CH_2)_5CO_2$H, $R^3$=cyclopentyl, X=combination of OH and H]

Melting point: 173–175° C. (decomposed); $^1$H-NMR δ ppm(DMSO-d$_6$): 1.35–1.77(15H,m), 1.95–2.08(1H,m), 2.21–2.25(2H,m), 4.10(3H,s), 4.12–4.16(4H,m), 6.83(1H, d), 7.24(1H,d), 7.71(1H,s), 8.16(1H,s)

Example 37

In a similar manner to Example 33, the following compound was obtained.

4-[2-(3-Cyclopentyl-3-hydroxy-1-propenyl)-4-methoxy-5-pyridyloxy]butanoic acid hydrochloride [in the formula (1), $R^1$=Me, $R^2$=—$(CH_2)_3CO_2$H, $R^3$=cyclopentyl, X=combination of OH and H]

Melting point: 168–169° C. (decomposed); $^1$H-NMR δ ppm(DMSO-d$_6$): 1.35–1.70(8H,m), 1.94–2.01(3H,m), 2.08 (1H,s), 2.37–2.41(2H,m), 4.10(3H,s), 4.15–4.19(3H,m), 6.84(1H,d), 7.24(1H,dd), 7.71(1H,s), 8.17(1H,s)

Example 38

In a similar manner to Example 33, the following compound was obtained.

6-[2-(3-Cyclopentyl-3-oxo-1-propenyl)-4-methoxy-5-pyridyloxy]hexanoic acid hydrochloride [in the formula (1), $R^1$=Me, $R^2$=—$(CH_2)_5CO_2$H, $R^3$=cyclopentyl, X=O]

Melting point: 145–148° C.; $^1$H-NMR δ ppm(DMSO-d$_6$): 1.40–1.93(14H,m), 2.31(2H,t), 3.23–3.31(1H,m), 4.06(3H, s), 4.18(2H,t), 7.53(1H,d), 7.72(1H,d), 7.88(1H,s), 8.34(1H, s)

Example 39

In a similar manner to Example 33, the following compound was obtained.

4-[5-Hydroxy-2-(3-hydroxy-1-octenyl)-4-pyridyloxy] butanoic acid hydrochloride [in the formula (1), $R^1$=—$(CH_2)_3CO_2$H, $R^2$=H, $R^3$=—$(CH_2)_4CH_3$, X=combination of OH and H]

Melting point: 190–191° C. (decomposed); $^1$H-NMR δ ppm(DMSO-d$_6$): 0.85–0.88(3H,m), 1.17–1.54(4H,m), 2.02–2.09(2H,m), 2.50–2.53(4H,m), 4.05–4.10(2H,m), 4.19–4.22(1H,m), 4.33–4.36(2H,m), 6.74(1H,d), 7.14(1H, dd), 7.66(1H,s), 8.10(1H,s)

Example 40

In a similar manner to Example 33, the following compound was obtained.

4-[2-(3-Hydroxy-1-octenyl)-5-methoxy-4-pyridyloxy] butanoic acid hydrochloride [in the formula (1), $R^1$=—$(CH_2)_3CO_2$H, $R^2$=Me, $R^3$=—$(CH_2)_4CH_3$, X=combination of OH and H]

Melting point: 163–165° C.; $^1$H-NMR δ ppm(DMSO-d$_6$): 0.85–0.89(3H,m), 1.17–1.53(6H,m), 2.46–2.51(4H,m), 3.95 (3H,s), 4.05–4.10(2H,m), 4.23–4.24(1H,m), 4.35–4.39(2H, m), 6.82(1H,d), 7.22(1H,dd), 7.72(1H,s), 8.16(1H,s)

Example 41

In a similar manner to Example 33, the following compound was obtained.

5-[2-(3-Hydroxy-1-octenyl)-4-methoxy-5-pyridyloxy] pentanoic acid hydrochloride [in the formula (1), $R^1$=Me, $R^2$=—$(CH_2)_4CO_2$H, $R^3$=—$(CH_2)_4CH_3$, X=combination of OH and H]

Melting point: 149–151° C.; $^1$H-NMR δ ppm(DMSO-d$_6$): 0.85–0.89(3H,m), 1.18–1.19(2H,m), 1.29–1.79(8H,m), 2.35–2.39(2H,m), 4.03–4.08(2H,m), 4.10(3H,s), 4.14–4.17 (2H,m), 4.22–4.26(1H,m), 6.82(1H,d), 7.21(1H,dd), 7.71 (1H,s), 8.17(1H,s)

Example 42

Synthesis of methyl 6-[5-methoxy-2-(3-oxo-3-phenyl-1-propenyl)-4-pyridyloxy]hexanoate [in the formula (1), $R^1=\text{—}(CH_2)_5CO_2Me$, $R^2=Me$, $R^3=Ph$, $X=O$]

In 5 ml of dimethylformamide, was dissolved 0.77 g (3.0 mmol) of 4-hydroxy-5-methoxy-2-(3-oxo-3-phenyl-1-propenyl)pyridine [in the formula (1), $R^1=H$, $R^2=Me$, $R^3=Ph$, $X=O$] which had been obtained in Example 19, followed by the addition of 0.75 g (0.36 mmol) of methyl 6-bromohexanoate and 0.50 g (0.36 mmol) of potassium carbonate. The resulting mixture was stirred over an oil bath of 60° C. for one hour. The reaction mixture was poured into cold water and extracted with ethyl acetate. The organic layer was washed with saturated saline, dried and then concentrated under reduced pressure. The residue was chromatographed on silica gel, whereby 1.03 g (yield: 90%) of the title compound were obtained as a pale yellow oil from a 1% (v/v) methanol-dichloromethane eluate fraction.
$^1$H-NMR δ ppm(CDCl$_3$): 1.51–1.56(2H,m), 1.69–1.75(2H,m), 1.87–1.93(2H,m), 2.35–2.39(2H,m), 3.68(3H,s), 3.99 (3H,s), 4.09–4.12(2H,m), 7.01(1H,s), 7.48–7.52(2H,m), 7.57–7.59(1H,m), 7.70(1H,d), 7.93(1H,d), 8.07–8.09(2H,m), 8.22(1H,s)

Example 43

Synthesis of 4-benzoyloxy-5-methoxy-2-(3-oxo-3-phenyl-1-propenyl)pyridine [in the formula (1), $R^1=\text{—}COPh$, $R^2=Me$, $R^3=Ph$, $X=O$]

In 8 ml of dichloromethane, was suspended 0.51 g (2.0 mmol) of 4-hydroxy-5-methoxy-2-(3-oxo-3-phenyl-1-propenyl)pyridine [in the formula (1), $R^1=H$, $R^2=Me$, $R^3=Ph$, $X=O$] which had been obtained in Example 19, followed by the addition of 0.31 g (2.2 mmol) of benzoyl chloride and 0.20 g (2.0 mmol) of triethylamine. The resulting mixture was stirred at room temperature for 3 hours. The reaction mixture was washed with a saturated aqueous solution of sodium bicarbonate, dried and then concentrated under reduced pressure. The residue was chromatographed on silica gel. The crystals obtained from a dichloromethane eluate fraction were recrystallized from ethyl acetate, whereby 0.64 g (yield: 89%) of the title compound was obtained.

Melting point: 179–180.5° C.; $^1$H-NMR δ ppm(CDCl$_3$): 3.99(3H,s), 7.41(1H,s), 7.48–7.61(5H,m), 7.66–7.70(1H,m), 7.74(1H,d), 7.96(1H,d), 8.07–8.09(2H,m), 8.19–8.22(2H,m), 8.47(1H,s)

Example 44

In a similar manner to Example 42, the following compound was obtained.
Ethyl 4-[5-methyoxy-2-(3-oxo-3-phenyl-1-propenyl)-4-pyridyloxy]butanoate [in the formula (1), $R^1=\text{—}(CH_2)_3CO_2Et$, $R^2=Me$, $R^3=Ph$, $X=O$]

Melting point: 65–66° C.; $^1$H-NMR δ ppm(CDCl$_3$): 1.26 (3H,t), 2.00–2.36(2H,m), 2.40–2.66(2H,m), 4.00 (3H,s), 4.02–4.32(4H,m), 7.12(1H,s), 7.40–7.64(3H,m), 7.70(1H,d), 8.00(1H,d), 8.04–8.20(2H,m), 8.26(1H,s)

Example 45

In a similar manner to Example 42, the following compound was obtained.
Ethyl 5-methoxy-2-(3-oxo-3-phenyl-1-propenyl)-4-pyridyloxy]acetate [in the formula (1), $R^1=\text{—}CH_2CO_2Et$, $R^2=Me$, $R^3=Ph$, $X=O$]

Melting point: 113–113.5° C.; $^1$H-NMR δ ppm(CDCl$_3$): 1.32(3H,t), 4.03(3H,s), 4.30(2H,q), 4.79(2H,s), 6.89(1H,s), 7.46–7.54(2H,m), 7.56–7.62(1H,m), 7.67(1H,s), 7.94(1H,d), 8.06–8.10(2H,m), 8.28(1H,s)

Example 46

In a similar manner to Example 42, the following compound was obtained.
4-Butoxy-5-methoxy-2-(3-oxo-3-phenyl-1-propenyl) pyridine [in the formula (1), $R^1=\text{—}(CH_2)_3CH_3$, $R^2=Me$, $R^3=Ph$, $X=O$]

Melting point: 80–81° C.; $^1$H-NMR δ ppm(CDCl$_3$) 1.00 (3H,t), 1.46–1.55(2H,m), 3.99(3H,s), 4.12(2H,t), 7.02(1H,s), 7.47–7.53(2H,m), 7.56–7.62(2H,m), 7.70(1H,d), 7.93 (1H,d), 8.06–8.11(2H,m), 8.22(1H,s)

Example 47

In a similar manner to Example 42, the following compound was obtained.
5-Methoxy-4-(2-oxo-2-phenylethoxy)-2-(3-oxo-3-phenyl-1-propenyl)pyridine [in the formula (1), $R^1=\text{—}CH_2COPh$, $R^2=Me$, $R^3=Ph$, $X=O$]

Melting point: 151–152° C.; $^1$H-NMR δ ppm(CDCl$_3$): 4.03(3H,s), 5.51(2H,s), 6.86(1H,s), 7.45–7.58(4H,m), 7.60 (1H,d), 7.64–7.70(2H,m), 7.90(1H,d), 7.98–8.04(4H,m), 8.28(1H,s)

Example 48

In a similar manner to Example 42, the following compound was obtained.
5-Methoxy-4-methoxyethoxymethoxy-2-(3-oxo-3-phenyl-1-propenyl)pyridine [in the formula (1), $R^1=\text{—}CH_2OCH_2CH_2OCH_3$, $R^2=Me$, $R^3=Ph$, $X=O$]

Melting point: 66–67° C.; $^1$H-NMR δ ppm(CDCl$_3$): 3.38 (3H,s), 3.54–3.59(2H,m), 3.85–3.90(2H,m), 4.02(3H,s), 5.44(2H,s), 7.38(1H,s), 7.48–7.54(2H,m), 7.56–7.62(1H,m), 7.72(1H,d), 7.92(1H,d), 8.06–8.10(2H,m), 8.27(1H,s)

Example 49

Synthesis of 4,5-dimethoxy-2-[3-(2-methoxyphenyl)-3-(oxo-1-propenyl]pyridine [in the formula (1), $R^1=R^2=Me$, $R^3=$2-methoxyphenyl, $X=O$]

In 90 ml of methanol, 5.01 g (30 mmol) of 4,5-dimethoxypyridine-2-aldehyde were dissolved, followed by the addition of 100 ml of a 10% aqueous solution of sodium hydroxide. While stirring at 0° C., a 10 ml methanol solution containing 4.50 g (30 mmol) of 2'-methoxyacetophenone was added dropwise to the reaction mixture. The resulting mixture was stirred at room temperature for 5 hours. The crystals so precipitated were collected by filtration, washed with water and recrystallized from acetone-isopropyl ether, whereby 8.10 g (yield: 90%) of the title compound were obtained.

Melting point: 131–132° C.; $^1$H-NMR δ ppm(CDCl$_3$): 3.90(3H,s), 3.96(3H,s), 4.00(3H,s), 7.04(1H,s), 6.98–7.05 (2H,m), 7.45–7.49(1H,m), 7.52(1H,d), 7.59–7.61(1H,m), 7.62(1H,d), 8.19(1H,s)

Example 50

In a similar manner to Example 49, the following compound was obtained.
4,5-Dimethoxy-2-[3-(4-methoxyphenyl)-3-oxo-1-propenyl] pyridine [in the formula (1), $R^1=R^2=Me$, $R^3=$4-methoxyphenyl, $X=O$]

Melting point: 99–100° C.; $^1$H-NMR δ ppm(CDCl$_3$): 3.90(3H,s), 3.98(3H,s), 4.01(3H,s), 6.97–7.00(2H,m), 7.03 (1H,s), 7.70(1H,d), 7.97(1H,d), 8.10–8.12(2H,m), 8.23(1H,s)

Example 51

In a similar manner to Example 49, the following compound was obtained.
4,5-Dimethoxy-2-[3-(2-nitrophenyl)-3-oxo-1-propenyl]pyridine [in the formula (1), $R^1=R^2=Me$, $R^3$=2-nitrophenyl, X=O]

Melting point: 170–172° C.; $^1$H-NMR δ ppm(CDCl$_3$): 3.96(3H,s), 3.99(3H,s), 7.06(1H,s), 7.18(1H,d), 7.24(1H,d), 7.51(1H,dd), 7.65(1H,td), 7.76(1H,td), 8.15(1H,s), 8.19(1H,dd)

Example 52

In a similar manner to Example 49, the following compound was obtained.
4,5-Dimethoxy-2-[3-(4-nitrophenyl)-3-oxo-1-propenyl]pyridine [in the formula (1), $R^1=R^2=Me$, $R^3$=4-nitrophenyl, X=O]

Melting point: 195–197° C.; $^1$H-NMR δ ppm(CDCl$_3$): 3.99(3H,s), 4.03(3H,s), 7.05(1H,s), 7.76(1H,d), 7.93(1H,d), 8.20(1H,s), 8.23(2H,d), 8.35(2H,d)

Example 53

In a similar manner to Example 49, the following compound was obtained.
4,5-Dimethoxy-2-[3-(2,4-dichlorophenyl)-3-oxo-1-propenyl]pyridine [in the formula (1), $R^1=R^2=Me$, $R^3$=2,4-dichlorophenyl, X=O]

Melting point: 165–166° C.; $^1$H-NMR δ ppm(CDCl$_3$): 3.96(3H,s), 4.00(3H,s), 7.04(1H,s), 7.36(1H,m), 7.38(1H,d), 7.39(1H,m), 7.45(1H,d), 7.48(1H,m), 8.20 (1H,s)

Example 54

In a similar manner to Example 49, the following compound was obtained.
4,5-Dimethoxy-2-[3-(2,6-dichlorophenyl)-3-oxo-1-propenyl]pyridine [in the formula (1), $R^1=R^2=Me$, $R^3$=2,6-dichlorophenyl, X=O]

Melting point: 166–168° C.; $^1$H-NMR δ ppm(CDCl$_3$): 3.97(3H,s), 4.00(3H,s), 6.97–7.00(2H,m), 7.09(1H,s), 7.16 (1H,d), 7.23(1H,d), 7.30–7.38(4H,m), 8.18(1H,s)

Example 55

In a similar manner to Example 49, the following compound was obtained.
5-Ethoxy-4-hydroxy-2-($^3$-oxo-3-phenyl-1-propenyl]pyridine [in the formula (1), $R^1$=H, $R^2$=Et, $R^3$=Ph, X=O]

Melting point: 103–105° C.; $^1$H-NMR δ ppm(DMSO-d$_6$): 1.34(3H,t), 4.14(2H,q), 7.12(1H,s), 7.56(1H,d), 7.70(1H,d), 7.40–8.10(6H,m)

Example 56

In a similar manner to Example 49, the following compound was obtained.
4-Hydroxy-5-methoxy-2-[3-(2,6-dimethoxyphenyl)-3-oxo-1-propenyl]pyridine [in the formula (1), $R^1$=H, $R^2$=Me, $R^3$=2,6-dimethoxyphenyl, X=O]

Melting point: 170–171° C.; $^1$H-NMR δ ppm(DMSO-d$_6$): 3.72(6H,s), 3.84(3H,s), 6.70(2H,d), 6.94(1H,s), 6.97(2H,s), 7.36(1H,t), 7.97(1H,s)

Example 57

In a similar manner to Example 49, the following compound was obtained.
4-Hydroxy-5-methoxy-2-[3-(2,5-dimethoxyphenyl)-3-oxo-1-propenyl]pyridine [in the formula (1), $R^1$=H, $R^2$=Me, $R^3$=2,5-dimethoxyphenyl, X=O]

Melting point: 185–187° C. (decomposed); $^1$H-NMR δ ppm (DMSO-d$_6$): 3.77(3H,s), 3.87(3H,s), 3.95(3H,s), 7.13 (3H,m), 7.40(1H,d), 7.63(1H,s), 7.80(1H,d), 8.19(1H,s)

Example 58

In a similar manner to Example 49, the following compound was obtained.
4-Hydroxy-5-methoxy-2-[3-(3,4-dimethoxyphenyl)-3-oxo-1-propenyl]pyridine hydrochloride [in the formula (1), $R^1$=H, $R^2$=Me, $R^3$=3,4-dimethoxyphenyl, X=O]

Melting point: 244–247° C. (decomposed); $^1$H-NMR δ ppm(DMSO-d$_6$): 3.89(3H,s), 3.95(3H,s), 4.00(3H,s), 7.15 (1H,d), 7.66(1H,d), 7.75(1H,d), 7.77(1H,s), 7.99(1H,dd), 8.22(1H,s), 8.64(1H,d)

Example 59

In a similar manner to Example 49, the following compound was obtained.
4-Hydroxy-5-methoxy-2-[3-(2,4-dimethoxyphenyl)-3-oxo-1-propenyl]pyridine [in the formula (1), $R^1$=H, $R^2$=Me, $R^3$=2,4-dimethoxyphenyl, X=O]

Melting point: 168–170° C.; $^1$H-NMR δ ppm(DMSO-d$_6$): 3.73(3H,s), 3.84(3H,s), 3.86(3H,s), 6.60(1H,s), 6.62–6.66 (2H,m), 7.20(1H,d), 7.44(1H,d), 7.52–7.54(1H,m), 7.70(1H,s)

Example 60

In a similar manner to Example 49, the following compound was obtained.
4-Hydroxy-5-methoxy-2-[3-(2-methoxyphenyl)-3-oxo-1-propenyl]pyridine [in the formula (1), $R^1$=H, $R^2$=Me, $R^3$=2-methoxyphenyl, X=O]

Melting point: 172–174° C.; $^1$H-NMR δ ppm(DMSO-d$_6$): 3.90(3H,s), 3.92(3H,s), 7.05–7.09(1H,m), 7.20–7.22(1H,m), 7.44(1H,d), 7.45(1H,s), 7.54–7.60(2H,m), 7.70(1H,d), 8.15 (1H,s)

Example 61

In a similar manner to Example 49, the following compound was obtained.
4-Hydroxy-5-methoxy-2-[3-oxo-3-(3,4,5-trimethoxyphenyl)-1-propenyl]pyridine hydrochloride [in the formula (1), $R^1$=H, $R^2$=Me, $R^3$=3,4,5-trimethoxyphenyl, X=O]

Melting point: 178–180° C. (decomposed); $^1$H-NMR δ ppm(DMSO-d$_6$): 3.79(3H,s), 3.93(6H,s), 3.97(3H,s), 7.50 (2H,s), 7.58(1H,s), 7.64(1H,d), 8.17(1H,s), 8.50(1H,d)

Example 62

In a similar manner to Example 49, the following compound was obtained.
4,5-Dimethoxy-2-[3-(2-furyl)-3-oxo-1-propenyl]pyridine [in the formula (1), $R^1=R^2=Me$, $R^3$=2-furyl, X=O]

Melting point: 159–160° C.; $^1$H-NMR δ ppm(CDCl$_3$): 3.97(3H,s), 4.01(3H,s), 6.59–6.61(1H,m), 7.04(1H,s), 7.39–7.40(1H,m), 7.67–7.68(1H,m), 7.79(2H,s), 8.23(1H,s)

Example 63

In a similar manner to Example 49, the following compound was obtained.
4,5-Dimethoxy-2-[3-oxo-3-(2-thienyl)-1-propenyl]pyridine [in the formula (1), $R^1=R^2=Me$, $R^3$=2-thienyl, X=O]

Melting point: 154–155° C.; $^1$H-NMR δ ppm(CDCl$_3$): 3.97(3H,s), 4.01(3H,s), 7.02(1H,s), 7.17–7.20(1H,m), 7.69–7.71(1H,m), 7.74(1H,d), 7.85(1H,d), 7.94–7.96(1H,m), 8.23(1H,s)

Example 64

In a similar manner to Example 49, the following compound was obtained.

4,5-Dimethoxy-2-[3-oxo-3-(3-thienyl)-1-propenyl]pyridine [in the formula (1), $R^1=R^2$=Me, $R^3$=3-thienyl, X=O]

Melting point: 111–112° C.; $^1$H-NMR δ ppm(CDCl$_3$): 3.97(3H,s), 4.01(3H,s), 7.02(1H,s), 7.27–7.40(2H,m), 7.66–7.77(2H,m), 8.22(1H,s), 8.26–8.28(1H,m)

Example 65

In a similar manner to Example 49, the following compound was obtained.

4-Hydroxy-5-methoxy-2-[3-oxo-3-(3-thienyl)-1-propenyl]pyridine [in the formula (1), $R^1$=H, $R^2$=Me, $R^3$=3-thienyl, X=O]

Melting point: 250–255° C. (decomposed); $^1$H-NMR δ ppm(DMSO-d$_6$): 3.70(3H,s), 6.51(1H,s), 7.37(1H,d), 7.58 (1H,dd), 7.59(1H,d), 7.60(1H,s), 7.63(1H,dd), 8.59(1H,dd)

Example 66

Synthesis of 4,5-dimethoxy-2-[3-oxo-3-(2-pyridyl)-1-propenyl]pyridine [in the formula (1), $R^1=R^2$=Me, $R^3$=2-pyridyl, X=O]

In 150 ml of benzene, were dissolved 2.51 g (15 mmol) of 4,5-dimethoxypyridin-2-aldehyde and 1.82 g (15 mmol) of 2-acetylpyridine, followed by the addition 1.5 ml of piperidine and 4.5 ml of acetic acid. The resulting mixture was refluxed for 7 hours under stirring. After cooling, the reaction mixture was added to a 2% aqueous solution of sodium bicarbonate, followed by extraction with ethyl acetate. The organic layer was washed with saturated saline, dried and then concentrated under reduced pressure. The crystals so precipitated were recrystallized from ethanol, whereby 2.47 g (yield: 61%) of the title compound were obtained.

Melting point: 158–160° C.; $^1$H-NMR δ ppm(CDCl$_3$): 4.00(3H,s), 4.01(3H,s), 7.19(1H,s), 7.50–7.57(1H,m), 7.80 (1H,d), 7.70–8.24(2H,m), 8.25(1H,s), 8.50(1H,d), 8.72–8.79(1H,m)

Example 67

In a similar manner to Example 66, the following compound was obtained.

4,5-Dimethoxy-2-[3-oxo-3-(3-pyridyl)-1-propenyl]pyridine [in the formula (1), $R^1=R^2$=Me, $R^3$=3-pyridyl, X=O]

Melting point: 157–158° C.; $^{11}$H-NMR δ ppm(CDCl$_3$): 3.99(3H,s), 4.03(3H,s), 7.05(1H,s), 7.38–7.52(1H,m), 7.70 (1H,d), 7.90(1H,d), 8.24(1H,s), 8.28–8.41(1H,m), 8.77–8.85(1H,m), 9.28–9.30(1H,m)

Example 68

In a similar manner to Example 66, the following compound was obtained.

4,5-Dimethoxy-2-[3-oxo-3-(4-pyridyl)-1-propenyl]pyridine [in the formula (1), $R^1=R^2$=Me, $R^3$=4-pyridyl, X=O]

Melting point: 146–147° C.; $^1$H-NMR δ ppm(CDCl$_3$): 3.99(3H,s), 4.02(3H,s), 7.05(1H,s), 7.70(1H,d), 7.80–7.85 (2H,m), 7.90(1H,d), 8.24(1H,s), 8.80–8.87(2H,m)

Example 69

In a similar manner to Example 66, the following compound was obtained.

Ethyl 6-[5-methoxy-2-(3-oxo-3-(2-pyridyl)-1-propenyl]-4-pyridyloxy]hexanoate [in the formula (1), $R^1$=—(CH$_2$)$_5$CO$_2$Et, $R^2$=Me, $R^3$=2-pyridyl, X=O]

Melting point: 74–74.5° C.; $^1$H-NMR δ ppm(CDCl$_3$): 1.26(3H,t), 1.50–2.00(6H,m), 2.36(2H,t), 3.99(3H,s), 4.00–4.30(4H,m), 7.16(1H,s), 7.42–7.57(1H,m), 7.87–7.98 (1H,m), 7.90(1H,d), 8.13–8.14(1H,m), 8.24(1H,s), 8.50(1H, d), 8.73–8.78(1H,m)

Example 70

In a similar manner to Example 66, the following compound was obtained.

Ethyl 4-[5-methoxy-2-(3-oxo-3-(2-pyridyl)-1-propenyl]-4-pyridyloxy]butanoate dihydrochloride [in the formula (1), $R^1$=—(CH$_2$)$_3$CO$_2$Et, $R^2$=Me, $R^3$=2-pyridyl, X=O]

Melting point: 144–146° C.; $^{11}$H-NMR δ ppm(DMSO-d$_6$): 1.20(3H,t), 2.08–2.13(2H,m), 2.50(2H,t), 4.04(3H,s), 4.09(2H,q), 4.47(2H,t), 7.75–7.79(1H,m), 8.03(1H,d), 8.10–8.14(2H,m), 8.16(1H,s), 8.43(1H,s), 8.74(1H,d), 8.83 (1H,d)

Example 71

In a similar manner to Example 66, the following compound was obtained.

Ethyl 4-[5-methoxy-2-(3-oxo-3-(3-pyridyl)-1-propenyl]-4-pyridyloxy]butanoate dihydrochloride [in the formula (1), $R^1$=—(CH$_2$)$_3$CO$_2$Et, $R^2$=Me, $R^3$=3-pyridyl, X=O]

Melting point: 172–174° C.; $^1$H-NMR δ ppm(DMSO-d$_6$): 1.20(3H,t), 2.07–2.14(2H,m), 2.51(2H,t), 4.03(3H,s), 4.09 (2H,q), 4.46(2H,t), 7.82–7.85(1H,m), 7.93(1H,d), 8.25(1H, s), 8.43(1H,s), 8.67(1H,d), 8.74(1H,d), 8.95–8.97(1H,m), 9.52(1H,d)

Example 72

In a similar manner to Example 66, the following compound was obtained.

Ethyl 4-[5-methoxy-2-(3-oxo-3-(4-pyridyl)-1-propenyl]-4-pyridyloxy]butanoate dihydrochloride [in the formula (1), $R^1$=—(CH$_2$)$_3$CO$_2$Et, $R^2$=Me, $R^3$=4-pyridyl, X=O]

Melting point: 174–176° C.; $^1$H-NMR δ ppm(DMSO-d$_6$): 1.19(3H,t), 2.07–2.14(2H,m), 2.51(2H,t), 4.04(3H,s), 4.08 (2H,q), 4.45(2H,t), 7.94(1H,d), 8.23(1H,s), 8.33–8.35(2H, m), 8.43(1H,s), 8.63(1H,d), 9.02–9.04(2H,m)

Example 73

In a similar manner to Example 1, the following compound was obtained.

2-(3-Cyclohexyl-3-oxo-1-propenyl)-4,5-dimethoxypyridine hydrochloride [in the formula (1), $R^1=R^2$=Me, $R^3$=cyclohexyl, X=O]

Melting point: 195–197° C.; $^{11}$H-NMR δ ppm(DMSO-d$_6$): 1.22–1.36(5H,m), 1.65–1.90(5H,m), 2.73(1H,m), 3.99 (3H,s), 4.09(3H,s), 7.61(1H,d), 7.68(1H,d), 7.93(1H,s), 8.73 (1H,s)

Example 74

In a similar manner to Example 1, the following compound was obtained.

2-(3-Cyclohexyl-3-oxo-1-propenyl)-4-cyclopentyloxy-5-methoxypyridine [in the formula (1), $R^1$=cyclopentyl, $R^2$=Me, $R^3$=cyclohexyl, X=O]

Melting point: 116–117° C.; $^1$H-NMR δ ppm(CDCl$_3$): 1.21–1.58(5H,m), 1.62–1.79(2H,m), 1.80–2.20(10H,m), 2.69(3H,m), 3.95(3H,s), 4.65(1H,s), 6.97(1H,s), 7.10(1H, d), 7.50(1H,d), 8.16(1H,s)

Example 75

In a similar manner to Example 1, the following compound was obtained.
2-(3-Cyclohexyl-3-oxo-1-propenyl)-4-hydroxy-5-methoxypyridine hydrochloride [in the formula (1), $R^1$=H, $R^2$=Me, $R^3$=cyclohexyl, X=O]

Melting point: 162–164° C.; $^1$H-NMR δ ppm(DMSO-$d_6$): 1.17–1.36(5H,m), 1.64–1.79(5H,m), 2.73(1H,m), 3.98(3H, s), 7.44(1H,d), 7.58(1H,d), 7.64(1H,s), 8.29 (1H,s)

Example 76

In a similar manner to Example 1, the following compound was obtained.
Ethyl 4-[2-(3-cyclohexyl-3-oxo-1-propenyl)-5-methoxy-4-pyridyloxy]butanoate hydrochloride [in the formula (1), $R^1$=—$(CH_2)_3CO_2Et$, $R^2$=Me, $R^3$=cyclohexyl, X=O]

Melting point: 162–164° C.; $^1$H-NMR δ ppm(DMSO-$d_6$): 1.19(3H,t), 1.24–1.34(SH,m), 1.65–1.90(5H,m), 2.07(2H, m), 2.47–2.51(4H,m), 2.73(1H,m), 3.99(3H,s), 4.07(2H,q), 4.37(2H,t), 7.62(1H,d), 7.68(1H,d), 7.95(1H,s), 8.37(1H,s)

Example 77

In a similar manner to Example 1, the following compound was obtained.
Ethyl 6-[2-(3-cyclohexyl-3-oxo-1-propenyl)-5-methoxy-4-pyridyloxy]hexanoate hydrochloride [in the formula (1), $R^1$=—$(CH_2)_5CO_2Et$, $R^2$=Me, $R^3$=cyclohexyl, X=O]

Melting point: 142–143° C.; $^1$H-NMR δ ppm(DMSO-$d_6$): 1.18(3H,t), 1.26–1.90(16H,m), 2.32(2H,t), 2.73(1H,m), 3.99 (3H,s), 4.05(2H,q), 4.33(2H,t), 7.61(1H,d), 7.68(1H,d), 7.93 (1H,s), 8.36(1H,s)

Example 78

In a similar manner to Example 66, the following compound was obtained. ps Ethyl 5-[2-(3-cyclohexyl-3-oxo-1-propenyl)-5-methoxy-4-pyridyloxy]pentanoate hydrochloride [in the formula (1), $R^1$=—$(CH_2)_4CO_2Et$, $R^2$=Me, $R^3$=cyclohexyl, X=O]

Melting point: 154–156° C.; $^{11}$H-NMR δ ppm(DMSO-$d_6$): 1.18(3H,t), 1.24–1.34(5H,m), 1.65–1.90(9H,m), 2.40 (2H,t), 2.73(1H,m), 3.99(3H,s), 4.06(2H,q), 4.35(2H,t), 7.62 (1H,d), 7.69(1H,d), 7.94(1H,s), 8.36(1H,s)

Example 79

In a similar manner to Example 1, the following compound was obtained.
Ethyl 4-[2-(3-cyclopentyl-3-oxo-1-propenyl)-5-methoxy-4-pyridyloxy]butanoate hydrochloride [in the formula (1), $R^1$=—$(CH_2)_3CO_2Et$, $R^2$=Me, $R^3$=cyclopentyl, X=O]

Melting point: 162–164° C.; $^1$H-NMR δ ppm(DMSO-$d_6$): 1.19(3H,t), 1.57–1.93(8H,m), 2.03–2.10(2H,m), 2.47–2.50 (2H,m), 3.26(1H,m), 3.98(3H,s), 4.07(2H,d), 4.35(2H,t), 7.52(1H,d), 7.68(1H,d), 7.90(1H,s), 8.36(1H,s)

Example 80

In a similar manner to Example 1, the following compound was obtained.
Ethyl 4-[2-(3-cyclobutyl-3-oxo-1-propenyl)-5-methoxy-4-pyridyloxy]butanoate hydrochloride [in the formula (1), $R^1$=—$(CH_2)_3CO_2Et$, $R^2$=Me, $R^3$=cyclobutyl, X=O]

Melting point: 166–168° C.; $^{11}$H-NMR δ ppm(DMSO-$d_6$): 1.19(3H,t), 1.78–1.82(1H,m), 1.97–2.09(3H,m), 2.17–2.25(4H,m), 2.46–2.52(2H,m), 3.69(1H,m), 3.96(3H, s), 4.07(2H,d), 4.31(2H,t), 7.22(1H,d), 7.52(1H,d), 7.78(1H, s), 8.36(1H,s)

Example 81

In a similar manner to Example 42, the following compound was obtained.
Ethyl [4-methoxy-6-(3-oxo-3-phenyl-1-propenyl)-3-pyridyloxy]acetate [in the formula (1), $R^1$=Me, $R^2$=—$CH_2CO_2Et$, $R^3$=Ph, X=O]

Melting point: 91–92° C.; $^1$H-NMR δ ppm(CDCl$_3$): 1.31 (3H,t), 3.98(3H,s), 4.29(2H,q), 4.77(2H,s), 7.05(1H,s), 7.48–7.52(2H,m), 7.57–7.61(1H,m), 7.70(1H,d), 7.97(1H, d), 8.06–8.09(2H,m), 8.19(1H,s)

Example 82

In a similar manner to Example 42, the following compound was obtained.
Ethyl 4-[4-methoxy-6-(3-oxo-3-phenyl-1-propenyl)-3-pyridyloxy]butanoate [in the formula (1), $R^1$=Me, $R^2$=—$(CH_2)_3CO_2Et$, $R^3$=Ph, X=O]

Melting point: 74–76° C.; $^1$H-NMR δ ppm(CDCl$_3$): 1.26 (3H,t), 2.18(2H,q), 2.55(2H,t), 3.95(3H,s), 4.16(2H,q), 4.20 (2H,t), 7.03(1H,s), 7.48–7.52(2H,m), 7.57–7.60(1H,m), 7.71(1H,d), 7.94(1H,d), 8.07–8.09(2H,m), 8.21(1H,s)

Example 83

In a similar manner to Example 42, the following compound was obtained.
Ethyl 6-[4-methoxy-6-(3-oxo-3-phenyl-1-propenyl)-3-pyridyloxy]hexanoate [in the formula (1), $R^1$=Me, $R^2$=—$(CH_2)_5CO_2Et$, $R^3$=Ph, X=O]

Melting point: 87–89° C.; $^1$H-NMR δ ppm(CDCl$_3$): 1.26 (3H,t), 1.51–1.57(2H,m), 1.68–1.75(2H,m), 1.85–1.92(2H, m), 2.34(2H,t), 3.95(3H,s), 4.07–4.16(2H,m), 7.03(1H,s), 7.48–7.52(2H,m), 7.58–7.60(1H,m), 7.71(1H,d), 7.94(1H, d), 8.07–8.09(2H,m), 8.20(1H,s)

Example 84

In a similar manner to Example 42, the following compound was obtained.
Ethyl 4-[5-ethoxy-2-(3-oxo-3-phenyl-1-propenyl)-4-pyridyloxy]butanoate hydrochloride [in the formula (1), $R^1$=—$(CH_2)_3CO_2Et$, $R^2$=Et, $R^3$=Ph, X=O]

Melting point: 144–146° C.; $^1$H-NMR δ ppm(DMSO-$d_6$): 1.19(3H,t), 1.39(3H,t), 2.10–2.20(2H,m), 2.50–2.60(2H,m), 4.09(2H,q), 4.28(2H,q), 4.39(2H,t), 7.59–7.62(2H,m), 7.63–7.74(1H,m), 7.78(1H,d), 8.06(1H,s), 8.17–8.19(2H, m), 8.39(1H,s), 8.43(1H,d)

Example 85

In a similar manner to Example 42, the following compound was obtained.
Ethyl 6-[5-methoxy-2-(3-(2,6-dimethoxyphenyl)-3-oxo-1-propenyl)-4-pyridyloxy]hexanoate hydrochloride [in the formula (1), $R^1$=—$(CH_2)_5CO_2Et$, $R^2$=Me, $R^3$=2,6-dimethoxyphenyl, X=O]

Melting point: 155–157° C.; $^1$H-NMR δ ppm(DMSO-$d_6$): 1.17(3H,t), 1.41–1.46(2H,m), 1.57–1.63(2H,m), 1.76–1.82 (2H,m), 2.31(2H,t), 3.75(6H,s), 3.97(3H,s), 4.06(2H,q), 4.29(2H,t), 6.78(2H,d), 7.37(1H,d), 7.43(1H,d), 7.55(1H,d), 7.91(1H,s), 8.34(1H,s)

Example 86

In a similar manner to Example 42, the following compound was obtained.
Ethyl 4-[5-methoxy-2-(3-(2,6-dimethoxyphenyl)-3-oxo-1-propenyl)-4-pyridyloxy]butanoate hydrochloride [in the formula (1), $R^1=-(CH_2)_3CO_2Et$, $R^2=Me$, $R^3$=2,6-dimethoxyphenyl, X=O]

Melting point: 146–148° C.; $^1$H-NMR δ ppm(DMSO-$d_6$): 1.18(3H,t), 2.02–2.06(2H,m), 2.46(2H,t), 3.74(6H,s), 3.98(3H,s), 4.06(2H,q), 4.33(2H,t), 6.78(2H,d), 7.37(1H,d), 7.43(1H,d), 7.56(1H,d), 7.93(1H,s), 8.35(1H,s)

Example 87

In a similar manner to Example 42, the following compound was obtained.
Ethyl 4-[5-methoxy-2-(3-(2,5-dimethoxyphenyl)-3-oxo-1-propenyl)-4-pyridyloxy]butanoate hydrochloride [in the formula (1), $R^1=-(CH_2)_3CO_2Et$, $R^2=Me$, $R^3$=2,5-dimethoxyphenyl, X=O]

Melting point: 150–152° C.; $^1$H-NMR δ ppm(DMSO-$d_6$): 1.18(3H,t), 2.02–2.06(2H,m), 2.47(2H,t), 3.77(3H,s), 3.83(3H,s), 3.99(3H,s), 4.07(2H,q), 4.36(2H,t), 7.08(1H,m), 7.17(2H,m), 7.59(1H,d), 7.93(1H,s), 7.97(1H,d), 8.35(1H,s)

Example 88

In a similar manner to Example 42, the following compound was obtained.
Ethyl 6-[5-methoxy-2-(3-(2,5-dimethoxyphenyl)-3-oxo-1-propenyl)-4-pyridyloxy]hexanoate hydrochloride [in the formula (1), $R^1=-(CH_2)_5CO_2Et$, $R^2=Me$, $R^3$=2,5-dimethoxyphenyl, X=O]

Melting point: 127–129° C.; $^1$H-NMR δ ppm(DMSO-$d_6$): 1.18(3H,t), 1.42–1.48(2H,m), 1.58–1.63(2H,m), 1.78–1.83(2H,m), 2.31(2H,t), 3.77(3H,s), 3.83(3H,s), 3.99(3H,s), 4.05(2H,q), 4.33(2H,t), 7.08(1H,m), 7.17(2H,m), 7.59(1H,d), 7.94(1H,s), 7.98(1H,d), 8.35(1H,s) Example 89

In a similar manner to Example 42, the following compound was obtained.
Ethyl 5-[5-methoxy-2-(3-(2,5-dimethoxyphenyl)-3-oxo-1-propenyl)-4-pyridyloxy]pentanoate [in the formula (1), $R^1=-(CH_2)_4CO_2Et$, $R^2=Me$, $R^3$=2,5-dimethoxyphenyl, X=O]

Melting point: 122–123° C.; $^1$H-NMR δ ppm(DMSO-$d_6$): 1.26(3H,t), 1.50–2.10(4H,m), 2.41(2H,t), 3.80(3H,s), 3.85(3H,s), 3.97(3H,s), 4.00–4.18(4H,m), 6.80–7.20(4H,m), 7.52(1H,d), 7.62(1H,d), 8.19(1H,s)

Example 90

In a similar manner to Example 42, the following compound was obtained.
Ethyl 6-[5-methoxy-2-(3-(3,4-dimethoxyphenyl)-3-oxo-1-propenyl)-4-pyridyloxy]hexanoate hydrochloride [in the formula (1), $R^1=-(CH_2)_5CO_2Et$, $R^2=Me$, $R^3$=3,4-dimethoxyphenyl, X=O]

Melting point: 147–149° C.; $^1$H-NMR δ ppm(DMSO-$d_6$): 1.18(3H,t), 1.44–1.48(2H,m), 1.59–1.65(2H,m), 1.82–1.86(2H,m), 2.33(2H,t), 3.89(3H,s), 4.01(3H,s), 4.03(3H,s), 4.06(2H,q), 4.38(2H,t), 7.15(1H,d), 7.67(1H,d), 7.75(1H,d), 7.99(1H,dd), 8.10(1H,s), 8.35(1H,s), 8.64(1H,d)

Example 91

In a similar manner to Example 42, the following compound was obtained.
Ethyl 4-[5-methoxy-2-(3-(2,4-dimethoxyphenyl)-3-oxo-1-propenyl)-4-pyridyloxy]butanoate hydrochloride [in the formula (1), $R^1=-(CH_2)_3CO_2Et$, $R^2=Me$, $R^3$=2,4-dimethoxyphenyl, X=O]

Melting point: 169–171° C.; $^1$H-NMR δ ppm(CDCl$_3$): 1.27(3H,t), 2.22–2.27(2H,m), 2.56(2H,t), 3.87(3H,s), 4.01(3H,s), 4.04(3H,s), 4.16(2H,q), 4.37(2H,t), 6.49–6.50(1H,m), 6.57(1H,dd), 7.28–7.31(1H,m), 7.49(1H,d), 7.88(1H,d), 8.25(1H,s), 8.61(1H,d)

Example 92

In a similar manner to Example 42, the following compound was obtained.
Ethyl 6-[5-methoxy-2-(3-(2,4-dimethoxyphenyl)-3-oxo-1-propenyl)-4-pyridyloxy]hexanoate hydrochloride [in the formula (1), $R^1=-(CH_2)_5CO_2Et$, $R^2=Me$, $R^3$=2,4-dimethoxyphenyl, X=O]

Melting point: 158–160° C.; $^1$H-NMR δ ppm(CDCl$_3$): 1.26(3H,t), 1.55–1.59(2H,m), 1.69–1.77(2H,m), 1.95–2.04(2H,m), 2.35(2H,t), 3.88(3H,s), 4.02(3H,s), 4.05(3H,s), 4.13(2H,q), 4.20–4.28(2H,m), 6.49–6.50(1H,m), 6.55–6.57(1H,m), 7.28(1H,s), 7.48(1H,d), 7.89(1H,d), 8.25(1H,s), 8.65(1H,d)

Example 93

In a similar manner to Example 42, the following compound was obtained.
Ethyl 4-[5-methoxy-2-(3-(2-methoxyphenyl)-3-oxo-7-propenyl)-4-pyridyloxy]butanoate hydrochloride [in the formula (1), $R^1=-(CH_2)_3CO_2Et$, $R^2=Me$, $R^3$=2-methoxyphenyl, X=O]

Melting point: 148–150° C.; $^1$H-NMR δ ppm(CDCl$_3$): 1.27(3H,t), 2.21–2.26(2H,m), 2.55(2H,t), 4.02(3H,s), 4.03(3H,s), 4.16(2H,q), 4.36(2H,t), 7.01–7.04(2H,m), 7.36(1H,s), 7.51–7.56(1H,m), 7.54(1H,d), 7.71–7.74(1H,m), 8.26(1H,s), 8.47(1H,d)

Example 94

In a similar manner to Example 42, the following compound was obtained.
Ethyl 6-[5-methoxy-2-(3-(2-methoxyphenyl)-3-oxo-1-propenyl)-4-pyridyloxy]hexanoate hydrochloride [in the formula (1), $R^1=-(CH_2)_5CO_2Et$, $R^2=Me$, $R^3$=2-methoxyphenyl, X=O]

Melting point: 114–116° C.; $^1$H-NMR δ ppm(CDCl$_3$): 1.26(3H,t), 1.52–1.58(2H,m), 1.69–1.76(2H,m), 1.93–1.97(2H,m), 2.36(2H,t), 4.01(3H,s), 4.04(3H,s), 4.13(2H,q), 4.26–4.29(2H,m), 7.01–7.04(2H,m), 7.22(1H,s), 7.49–7.53(1H,m), 7.52(1H,d), 7.72–7.74(1H,m), 8.25(1H,s), 8.50(1H,d)

Example 95

In a similar manner to Example 42, the following compound was obtained.
Ethyl 5-[5-methoxy-2-(3-(2-methoxyphenyl)-3-oxo-1-propenyl)-4-pyridyloxy]pentanoate hydrochloride [in the formula (1), $R^1=-(CH_2)_4CO_2Et$, $R^2=Me$, $R^3$=2-methoxyphenyl, X=O]

Melting point: 101–102° C.; $^1$H-NMR δ ppm(CDCl$_3$): 1.26(3H,t), 1.84–1.97(4H,m), 2.42(2H,t), 4.02(3H,s), 4.04(3H,s), 4.14(2H,q), 4.31(2H,br), 7.00–7.04(2H,m), 7.28(1H,s), 7.49–7.55(1H,m), 7.51(1H,d), 7.72–7.73(1H,m), 8.25(1H,s), 8.51(1H,d)

Example 96

In a similar manner to Example 42, the following compound was obtained.
Ethyl 7-[5-methoxy-2-(3-(2-methoxyphenyl)-3-oxo-1-propenyl)-4-pyridyloxy]heptanoate hydrochloride [in the formula (1), $R^1=-(CH_2)_6CO_2Et$, $R^2=Me$, $R^3$=2-methoxyphenyl, X=O]

Melting point: 111–113° C.; $^1$H-NMR δ ppm(CDCl$_3$): 1.26(3H,t), 1.42–1.54(4H,m), 1.65–1.69(2H,m), 1.91–1.95

(2H,m), 2.32(2H,t), 4.02(3H,s), 4.04(3H,s), 4.13(2H,q), 4.26–4.29(2H,m), 7.00–7.04(2H,m), 7.25(1H,s), 7.50–7.55 (1H,m), 7.53(1H,d), 7.73(1H,dd), 8.25(1H,s), 8.52(1H,d).

Example 97

In a similar manner to Example 42, the following compound was obtained.
Ethyl 12-[5-methoxy-2-(3-(2-methoxyphenyl)-3-oxo-1-propenyl)-4-pyridyloxy]dodecanoate hydrochloride [in the formula (1), $R^1$=—$(CH_2)_{11}CO_2Et$, $R^2$=Me, $R^3$=2-methoxyphenyl, X=O]

Melting point: 80–82° C.; $^1$H-NMR δ ppm(CDCl$_3$): 1.17 (3H,t), 1.25–1.52(16H,m), 1.76–1.81(2H,m), 2.25(2H,t), 3.88(3H,s), 3.98(3H,s), 4.03(2H,q), 4.30(2H,t), 7.09(1H,t), 7.23(1H,d), 7.56(1H,d), 7.53–7.61(2H,m), 7.90(1H,s), 7.93 (1H,d), 8.35(1H,s)

Example 98

In a similar manner to Example 42, the following compound was obtained.
Ethyl 8-[5-methoxy-2-(3-(2-methoxyphenyl)-3-oxo-1-propenyl)-4-pyridyloxy]octanoate hydrochloride [in the formula (1), $R^1$=—$(CH_2)_7CO_2Et$, $R^2$=Me, $R^3$=2-methoxyphenyl, X=O]

Melting point: 102–104° C.; $^1$H-NMR δ ppm(CDCl$_3$): 1.17(3H,t), 1.29–1.41(4H,m), 1.49–1.57(2H,m), 1.75–1.82 (2H,m), 2.27(2H,t), 3.87(3H,s), 3.98(3H,s), 4.03(2H,q), 4.30(2H,t), 7.09(1H,t), 7.23(1H,d), 7.53(1H,d), 7.51–7.61 (2H,m), 7.88(1H,s), 7.90(1H,d), 8.35(1H,s)

Example 99

In a similar manner to Example 42, the following compound was obtained.
Methyl 4-[5-methoxy-2-(3-(2-methoxyphenyl)-3-oxo-1-propenyl)-4-pyridyloxy]benzoate [in the formula (1), $R^1$=4-methoxycarbonylbenzyloxy, $R^2$=Me, $R^3$=2-methoxyphenyl, X=O]

Melting point: 159–161° C.; $^1$H-NMR δ ppm(CDCl$_3$): 3.94(3H,s), 4.01(3H,s), 4.04(3H,s), 5.47(2H,s), 6.98–7.01 (2H,m), 7.40(1H,s), 7.47(1H,d), 7.48–7.49(4H,m), 7.69–7.72(1H,m), 8.09(2H,d), 8.26(1H,s), 8.48(1H,d)

Example 100

In a similar manner to Example 42, the following compound was obtained.
Ethyl 6-[5-methoxy-2-(3-oxo-3-(3-thienyl)-1-propenyl)-4-pyridyloxy]hexanoate hydrochloride [in the formula (1), $R^1$=—$(CH_2)_5CO_2Et$, $R^2$=Me, $R^3$=3-thienyl, X=O]

Melting point: 171–173° C.; $^1$H-NMR δ ppm(DMSO-d$_6$): 1.26(3H,t), 1.51-1.59(2H,m), 1.70–1.77(2H,m), 1.92–1.99 (2H,m), 2.36(2H,t), 4.03(3H,s), 4.13(2H,q), 4.29(2H,t), 7.24 (1H,s), 7.35–7.37(1H,m), 7.51(1H,d), 7.75–7.76(1H,m), 8.19(1H,s), 9.02–9.03(1H,m), 9.10(1H,d)

Example 101

In a similar manner to Example 42, the following compound was obtained.
Ethyl 6-[5-methoxy-2-(3-oxo-3-(3,4,5-trimethoxyphenyl)-1-propenyl)-4-pyridyloxy]hexanoate hydrochloride [in the formula (1), $R^1$=—$(CH_2)_5CO_2Et$, $R^2$=Me, $R^3$=3,4,5-trimethoxyphenyl, X=O]

Melting point: 129–130° C.; $^{11}$H-NMR δ ppm(CDCl$_3$): 1.26(3H,t), 1.53–1.59(2H,m), 1.70–1.75(2H,m), 1.94–1.98 (2H,m), 2.36(2H,t), 3.95(3H,s), 4.04(3H,s), 4.05(6H,s), 4.14 (2H,q), 4.27(2H,t), 7.17(1H,s), 7.53(1H,s), 7.65(2H,s), 8.20 (1H,s), 9.25(1H,d)

Example 102

In a similar manner to Example 42, the following compound was obtained.
6-[5-Methoxy-2-(3-oxo-3-(3,4,5-trimethoxyphenyl)-1-propenyl)-4-pyridyloxy]hexyl alcohol hydrochloride [in the formula (1), $R^1$=—$(CH_2)_6OH$, $R^2$=Me, $R^3$=3,4,5-trimethoxyphenyl, X=O]

Melting point: 188–190° C.; $^1$H-NMR δ ppm(CDCl$_3$): 1.28–1.66(6H,m), 1.93–2.08(2H,m), 3.68(2H,t), 3.95(3H,s), 4.05(3H,s), 4.06(6H,s), 4.28(2H,t), 7.15(1H,s), 7.54(1H,d), 7.66(2H,s), 8.21(1H,s), 9.24 (1H,d)

Example 103

In a similar manner to Example 33, the following compound was obtained.
6-[5-Methoxy-2-(3-oxo-3-phenyl-1-propenyl)-4-pyridyloxy]hexanoic acid [in the formula (1), $R^1$=$(CH_2)_5CO_2H$, $R^2$=Me, $R^3$=Ph, X=O]

Melting point: 148–150° C.; $^1$H-NMR δ ppm(DMSO-d$_6$): 1.41–1.48(2H,m), 1.55–1.74(2H,m), 1.78–1.81(2H,m), 2.24 (2H,t), 3.30(1H,br), 3.91(3H,s), 4.14(2H,t), 7.56–7.69(4H, m), 7.60(1H,d), 7.97(1H,d), 8.06–8.08(2H,m), 8.27(1H,s)

Example 104

In a similar manner to Example 33, the following compound was obtained.
4-[5-Ethoxy-2-(3-oxo-3-phenyl-1-propenyl)-4-pyridyloxy]butanoic acid hydrochloride [in the formula (1), $R^1$=—$(CH_2)_3CO_2H$, $R^2$=Et, $R^3$=Ph, X=O]

Melting point: 173–175° C.; $^1$H-NMR δ ppm(DMSO-d$_6$): 1.39(3H,t), 2.03–2.06(2H,m), 2.44(2H,t), 4.26(2H,q), 4.35 (2H,t), 7.60–7.64(2H,m), 7.72(1H,m), 7.73(1H,d), 7.99(1H, s), 8.14–8.17(2H,m), 8.32(1H,d), 8.37(1H,s)

Example 105

In a similar manner to Example 33, the following compound was obtained.
6-[5-Methoxy-2-(3-(2-methoxyphenyl)-3-oxo-1-propenyl)-4-pyridyloxy]hexanoic acid [in the formula (1), $R^1$=—$(CH_2)_5CO_2H$, $R^2$=Me, $R^3$=2-methoxyphenyl, X=O]

Melting point: 182–184° C.; $^1$H-NMR δ ppm(DMSO-d$_6$): 1.42–1.48(2H,m), 1.55–1.61(2H,m), 1.79–1.83(2H,m), 2.24 (2H,t), 3.88(3H,s), 3.99(3H,s), 4.33(2H,t), 7.09(1H,t), 7.22 (1H,d), 7.54–7.62(2H,m), 7.59(1H,d), 7.94(1H,s), 8.00(1H, d), 8.35(1H,s)

Example 106

In a similar manner to Example 33, the following compound was obtained.
4-[2-(3-Cyclohexyl-3-oxo-1-propenyl)-5-methoxy-4-pyridyloxy]butanoic acid [in the formula (1), $R^1$=—$(CH_2)_3CO_2H$, $R^2$=Me, $R^3$=cyclohexyl, X=O]

Melting point: 150–151° C.; $^1$H-NMR δ ppm(DMSO-d$_6$): 1.17–1.39(5H,m), 1.64–1.83(5H,m), 1.98(2H,m), 2.39(2H, t), 2.76(1H,m), 3.89(3H,s), 4.13(2H,t), 7.13(1H,d), 7.46(1H, d), 7.47(1H,s), 8.22(1H,s), 12.1(1H,br)

Example 107

Synthesis of 4,5-dimethoxy-2-(3-oxo-3-piperidino-1-propenyl)pyridine hydrochloride [in the formula (1), $R^1$=$R^2$=Me, $R^3$=piperidino, X=O]

In 30 ml of dimethylformamide, were dissolved 1.38 g (5.6 mmol) of 3-(4,5-dimethoxy-2-pyridyl)acrylic acid and 0.57 g (6.6 mmol) of piperidine. To the resulting solution, 0.66 g (6.6 mmol) of triethylamine, 1.83 g (6.6 mmol) of diphenyl phosphorylazide and 1.14 g (11.4 mmol) of triethylamine were successively added dropwise at 0° C. under stirring. The resulting mixture was then stirred at 0° C. for one hour and at room temperature for 3 hours. The reaction mixture was poured into ice water, extracted with ethyl acetate, washed with water, dried and then concentrated under reduced pressure. The residue was dissolved in ethyl acetate. To the resulting solution, a 4N HCl-ethyl acetate solution was added dropwise until the completion of the crystal precipitation. The crystals so precipitated were collected by filtration and dried, whereby 1.54 g (yield: 88%) of the title compound were obtained.

Melting point: 185–186° C.; $^1$H-NMR δ ppm(DMSO-$d_6$): 1.54–1.65(6H,m), 3.56–3.70(4H,m), 3.98(3H,s), 4.11(3H,s), 7.57(1H,d), 7.92(1H,d), 7.94(1H,s), 8.31 (1H,s)

Example 108

In a similar manner to Example 107, the following compound was obtained.
4,5-Dimethoxy-2-(3-oxo-3-pyrrolidino-1-propenyl)pyridine hydrochloride [in the formula (1), $R^1=R^2$=Me, $R^3$=pyrrolidino, X=O]

Melting point: 204–204.5° C.; $^1$H-NMR δ ppm(DMSO-$d_6$): 1.83–1.88(2H,m), 1.92–1.96(2H,m), 3.43(2H,t), 3.71 (2H,t), 3.99(3H,s), 4.11(3H,s), 7.58(1H,d), 7.72(1H,d), 7.95 (1H,s), 8.32(1H,s)

Example 109

In a similar manner to Example 107, the following compound was obtained.
4,5-Dimethoxy-2-[3-(1-azepanyl)-3-oxo-1-propenyl]pyridine hydrochloride [in the formula (1), $R^1=R^2$=Me, $R^3$=1-azepanyl, X=O]

Melting point: 194–195° C.; $^1$H-NMR δ ppm(DMSO-$d_6$): 1.51–1.52(4H,m), 1.66–1.73(4H,m), 3.54(2H,t), 3.73(2H,t), 3.99(3H,s), 4.10(3H,s), 7.58(1H,d), 7.92(1H,d), 7.93(1H,s), 8.29(1H,s)

Example 110

In a similar manner to Example 107, the following compound was obtained.
4,5-Dimethoxy-2-(3-morpholino-3-oxo-1-propenyl)pyridine hydrochloride [in the formula (1), $R^1=R^2$=Me, $R^3$=morpholino, X=O]

Melting point: 205–207° C.; $^1$H-NMR δ ppm(DMSO-$d_6$): 3.62–3.77(8H,m), 3.98(3H,s), 4.09(3H,s), 7.61(1H,d), 7.90 (1H,d), 7.95(1H,s), 8.32(1H,s)

Example 111

In a similar manner to Example 107, the following compound was obtained.
4-Cyclopentyloxy-5-methoxy-2-(3-oxo-3-piperidino-1-propenyl)pyridine hydrochloride [in the formula (1), $R^1$=cyclopentyl, $R^2$=Me, $R^3$=piperidino, X=O]

Melting point: 178–179° C.; $^1$H-NMR δ ppm(DMSO-$d_6$): 1.54–1.81(12H,m), 2.06–2.09(2H,m), 3.56–3.70(4H,m), 3.97(3H,s), 5.27–5.29(1H,m), 7.57(1H,d), 7.89(1H,s), 7.98 (1H,d), 8.26(1H,s)

Test 1: Test on the inhibition of IL-4 production

Into individual wells of a 48-well microplate, the human T-cell strain ATL-16T(−) was poured at a concentration of $1 \times 10^6$ cells/0.5 ml/well (n=3), followed by the addition of a stimulator (20 nM of PMA) and a medicament at the same time. The resulting mixture was incubated in 5% $CO_2$ at 37° C. for 48 hours. After incubation, 100 μl of the supernatant were collected and subjected to measurement by a human IL-4 EIA kit (R&D SYSTEMS, INC.). The inhibition rate was calculated according to the following formula. The results are shown in Table 1.

$$\text{Inhibition rate (\%)} = \frac{\begin{array}{c}\text{(production amount of IL-4 when a}\\\text{stimulator was added)} - \text{(production}\\\text{amount of IL-4 when a stimulator}\\\text{and a medicament were added)}\end{array}}{\begin{array}{c}\text{(production amount of IL-4 when a}\\\text{stimulator was added)} - \text{(production}\\\text{amount of IL-4 when a stimulator}\\\text{was not added)}\end{array}} \times 100$$

TABLE 1

| | Inhibition rate (%) of IL-4 production | | | |
|---|---|---|---|---|
| Comp'd | $10^{-8}$M | $10^{-7}$M | $10^{-6}$M | $10^{-5}$M |
| Ex. 1 | 59.9 | 80.3 | 87.9 | 97.5 |
| Ex. 2 | 82.8 | 93.5 | 102.9 | 113.4 |
| Ex. 3 | 60.0 | 75.9 | 81.1 | 98.9 |
| Ex. 4 | 57.4 | 67.9 | 75.2 | 86.2 |
| Ex. 5 | 50.9 | 74.0 | 90.0 | 104.3 |
| Ex. 6 | 58.8 | 75.2 | 86.1 | 101.5 |
| Ex. 7 | 63.9 | 76.4 | 79.8 | 91.8 |
| Ex. 8 | 60.2 | 76.2 | 88.0 | 94.3 |
| Ex. 9 | 70.7 | 86.5 | 92.7 | 94.6 |
| Ex. 10 | 47.8 | 83.2 | 83.5 | 93.6 |
| Ex. 11 | 78.9 | 79.6 | 87.2 | 94.1 |
| Ex. 12 | 43.0 | 52.9 | 61.6 | 78.6 |
| Ex. 13 | 62.3 | 68.7 | 77.0 | 87.9 |
| Ex. 15 | 49.1 | 55.9 | 58.9 | 76.8 |
| Ex. 16 | 76.8 | 81.6 | 82.1 | 90.1 |
| Ex. 17 | 74.7 | 88.6 | 92.8 | 110.6 |
| Ex. 18 | 34.8 | 67.8 | 78.3 | 88.2 |
| Ex. 19 | 83.8 | 95.1 | 98.1 | 106.2 |
| Ex. 20 | 84.0 | 90.6 | 96.4 | 97.9 |
| Ex. 21 | 72.5 | 80.1 | 90.3 | 97.3 |
| Ex. 22 | 50.0 | 67.6 | 75.5 | 111.2 |
| Ex. 23 | 64.7 | 64.9 | 80.7 | 88.0 |
| Ex. 24 | 56.0 | 69.5 | 79.5 | 92.2 |
| Ex. 30 | 40.7 | 56.8 | 67.0 | 74.0 |
| Ex. 31 | 40.4 | 58.0 | 69.5 | 81.2 |
| Ex. 33 | 86.1 | 90.0 | 93.9 | 106.6 |
| Ex. 35 | 64.3 | 82.5 | 89.3 | 90.3 |
| Ex. 36 | 37.6 | 68.6 | 78.9 | 85.1 |
| Ex. 38 | 42.4 | 59.0 | 68.9 | 76.3 |
| Ex. 43 | 35.5 | 70.3 | 72.6 | 80.8 |
| Ex. 44 | 46.5 | 56.2 | 86.1 | 89.1 |
| Ex. 45 | 74.0 | 80.1 | 86.4 | 89.5 |
| Ex. 46 | 11.8 | 33.8 | 69.1 | 76.6 |
| Ex. 47 | 58.9 | 74.1 | 89.6 | 113.1 |
| Ex. 48 | 7.6 | 50.1 | 74.7 | 111.3 |

Test 2: Test on the inhibition of IL-4 production

Into individual wells of a 48-well microplate, the human T-cell strain ATL-16T(−) was poured at a concentration of $5 \times 10^5$ cells/0.5 ml/well (n=3), followed by the addition of a stimulator (20 nM of PMA) and a medicament at the same time. The resulting mixture was incubated in 5% $CO_2$ at 37° C. for 48 hours. After incubation, 50 μl of the supernatant were collected and subjected to measurement by a human IL-4 EIA kit (BIO SOURCE, INC.). The inhibition rate was calculated according to the following formula. The results are shown in Table 2.

$$\text{Inhibition rate (\%)} = \frac{\text{(production amount of IL-4 when a stimulator was added)} - \text{(production amount of IL-4 when a stimulator and a medicament were added)}}{\text{(production amount of IL-4 when a stimulator was added)} - \text{(production amount of IL-4 when a stimulator was not added)}} \times 100$$

$$\text{Inhibition rate (\%)} = \frac{\text{(production amount of IL-5 when a stimulator was added)} - \text{(production amount of IL-5 when the stimulator and a medicament were added)}}{\text{(production amount of IL-5 when the stimulator was added)} - \text{(production amount of IL-5 when the stimulator was not added)}} \times 100$$

TABLE 2

| Comp'd | Inhibition rate (%) of IL-4 production | | | |
|---|---|---|---|---|
| | $10^{-8}$M | $10^{-7}$M | $10^{-6}$M | $10^{-5}$M |
| Ex. 51 | 26.3 | 30.1 | 20.5 | 102.2 |
| Ex. 52 | 11.6 | 25.6 | 48.9 | 76.1 |
| Ex. 53 | 23.1 | 16.7 | 102.8 | 105.1 |
| Ex. 54 | 6.1 | 24.2 | 98.7 | 101.0 |
| Ex. 56 | 42.1 | 47.1 | 53.7 | 101.3 |
| Ex. 70 | 60.0 | 64.0 | 64.3 | 65.7 |
| Ex. 71 | 61.9 | 68.6 | 69.1 | 81.2 |
| Ex. 72 | 68.8 | 69.1 | 73.7 | 75.4 |
| Ex. 73 | 11.9 | 21.4 | 51.3 | 86.9 |
| Ex. 74 | 5.9 | 27.7 | 32.4 | 81.6 |
| Ex. 76 | 67.7 | 69.1 | 70.5 | 75.3 |
| Ex. 77 | 64.5 | 65.0 | 66.0 | 68.6 |
| Ex. 78 | 68.2 | 68.5 | 70.8 | 71.1 |
| Ex. 85 | 73.9 | 77.1 | 77.4 | 86.3 |
| Ex. 86 | 73.6 | 77.6 | 80.1 | 94.6 |
| Ex. 87 | 69.3 | 72.2 | 73.4 | 78.3 |
| Ex. 88 | 68.0 | 71.7 | 74.4 | 74.2 |
| Ex. 90 | 43.2 | 28.6 | 26.4 | 25.3 |
| Ex. 91 | 59.8 | 62.2 | 62.3 | 93.4 |
| Ex. 92 | 25.3 | 31.0 | 48.4 | 54.2 |
| Ex. 94 | 62.3 | 66.5 | 70.4 | 74.4 |
| Ex. 95 | 57.3 | 59.2 | 60.9 | 105.3 |
| Ex. 96 | 78.2 | 78.6 | 76.2 | 101.6 |
| Ex. 98 | 75.7 | 76.1 | 85.6 | 100.3 |
| Ex. 105 | 68.7 | 69.6 | 70.9 | 100.8 |
| Ex. 106 | 8.6 | 9.4 | 31.7 | 75.6 |

Test 3: Test on the inhibition of IL-5 production

The peripheral blood was collected from a normal volunteer and peripheral blood mononuclear cells (PBMC) of the human peripheral blood were separated therefrom by the specific gravity centrifugation method. They were suspended in an AIM-V medium and their cell count was adjusted. To individual wells of a 96-well incubation plate, $1 \times 10^6$ cells/ml of PBMC were poured, followed by the addition of a stimulator (10 µg/ml of ConA) and a medicament. The resulting mixture was incubated in 5% $CO_2$ at 37° C. for 48 hours. After incubation, 50 µl of the supernatant were collected and subjected to measurement by a human IL-5 EIA kit (BIO SOURCE, INC.). The inhibition rate was calculated according to the following formula. The results are shown in Table 3.

TABLE 3

| Compound | Inhibition rate (%) $10^{-6}$M | Compound | Inhibition rate (%) $10^{-6}$M |
|---|---|---|---|
| Ex. 1 | 95.3 | Ex. 36 | 86.5 |
| Ex. 2 | 93.4 | Ex. 37 | 72.6 |
| Ex. 3 | 65.8 | Ex. 38 | 88.7 |
| Ex. 4 | 60.2 | Ex. 39 | 97.6 |
| Ex. 5 | 89.3 | Ex. 40 | 97.5 |
| Ex. 6 | 67.0 | Ex. 41 | 91.0 |
| Ex. 7 | 94.2 | Ex. 42 | 77.5 |
| Ex. 8 | 75.3 | Ex. 43 | 61.4 |
| Ex. 9 | 82.5 | Ex. 44 | 90.6 |
| Ex. 10 | 62.9 | Ex. 45 | 64.3 |
| Ex. 11 | 77.3 | Ex. 46 | 86.9 |
| Ex. 12 | 72.4 | Ex. 47 | 67.2 |
| Ex. 13 | 80.9 | Ex. 48 | 62.2 |
| Ex. 14 | 90.2 | Ex. 49 | 65.0 |
| Ex. 15 | 79.2 | Ex. 50 | 79.4 |
| Ex. 16 | 79.4 | Ex. 51 | 93.6 |
| Ex. 17 | 84.3 | Ex. 52 | 64.2 |
| Ex. 18 | 96.9 | Ex. 53 | 75.0 |
| Ex. 19 | 94.8 | Ex. 54 | 93.3 |
| Ex. 20 | 92.8 | Ex. 55 | 97.5 |
| Ex. 21 | 67.3 | Ex. 56 | 79.8 |
| Ex. 22 | 80.9 | Ex. 57 | 82.5 |
| Ex. 23 | 96.3 | Ex. 58 | 91.3 |
| Ex. 24 | 80.0 | Ex. 59 | 78.9 |
| Ex. 25 | 97.5 | Ex. 60 | 91.4 |
| Ex. 26 | 83.7 | Ex. 61 | 79.4 |
| Ex. 27 | 89.6 | Ex. 62 | 72.3 |
| Ex. 28 | 72.1 | Ex. 63 | 81.0 |
| Ex. 29 | 99.8 | Ex. 64 | 82.1 |
| Ex. 30 | 73.2 | Ex. 65 | 77.2 |
| Ex. 31 | 71.6 | Ex. 66 | 70.1 |
| Ex. 32 | 80.7 | Ex. 67 | 77.9 |
| Ex. 33 | 72.1 | Ex. 68 | 95.4 |
| Ex. 34 | 61.0 | Ex. 69 | 73.1 |
| Ex. 35 | 82.2 | Ex. 70 | 81.4 |
| Ex. 71 | 93.3 | Ex. 91 | 85.8 |
| Ex. 72 | 84.1 | Ex. 92 | 96.4 |
| Ex. 73 | 82.3 | Ex. 93 | 66.0 |
| Ex. 74 | 77.9 | Ex. 94 | 95.2 |
| Ex. 75 | 90.6 | Ex. 95 | 65.6 |
| Ex. 76 | 91.2 | Ex. 96 | 79.8 |
| Ex. 77 | 82.0 | Ex. 97 | 93.9 |
| Ex. 78 | 63.1 | Ex. 98 | 96.8 |
| Ex. 79 | 64.1 | Ex. 99 | 80.3 |
| Ex. 80 | 69.2 | Ex. 100 | 82.6 |
| Ex. 81 | 72.7 | Ex. 101 | 95.6 |
| Ex. 82 | 69.6 | Ex. 102 | 97.3 |
| Ex. 83 | 96.2 | Ex. 103 | 72.4 |
| Ex. 84 | 89.4 | Ex. 104 | 89.3 |
| Ex. 85 | 75.7 | Ex. 105 | 71.0 |
| Ex. 86 | 71.9 | Ex. 106 | 78.7 |
| Ex. 87 | 90.2 | Ex. 107 | 71.9 |
| Ex. 88 | 61.6 | Ex. 108 | 78.5 |
| Ex. 89 | 82.1 | Ex. 109 | 83.8 |
| Ex. 90 | 75.6 | Ex. 110 | 79.3 |
| | | Ex. 111 | 73.2 |

Test 4: Test on the inhibition of IgE production

To a Balb/c mouse, the DNP-labeled ascaris antigen (5 μg) and Alum (1 mg) were intraperitoneally administered on Day 1 and Day 6 to sensitize the mouse with the antibody. From Day 1 to Day 10, a medicament was orally administered at a dose of 100 mg/kg once a day. On Day 11, the mouse was subjected to splenectomy and the spleen so obtained was untangled into its cells. To $5\times10^7$ cells/ml of the spleen cells so obtained, DNP-BSA (5 μg/ml) was added, followed by incubation at 37° C. for 24 hours. After incubation, 100 μl of the supernatant were collected and subjected to the measurement an IgE measuring kit (Yamasa Co., Ltd.). In order to determine IgG1, IgG2a and IgM, the absorbance of the incubated supernatant was measured by the EIA method and provided for comparison. The inhibition rate of IgE production was calculated according to the below-described formula. Inhibition rates of the IgG1, IgG2a and IgM production were similarly calculated, respectively. The results are shown in Table 4.

$$\text{Inhibition rate (\%)} = \frac{[\text{amount of IgE (O.D. value) when the mouse was sensitized}] - [\text{Amount of IgE (O.D. value) when the mouse was sensitized and administered with a medicament}]}{[\text{amount of IgE (O.D. value) when the mouse was sensitized}] - [\text{amount of IgE (O.D. value) when the mouse was not sensitized}]} \times 100$$

TABLE 4

| Comp'd | Inhibition rate (%) | | | |
|---|---|---|---|---|
|  | IgE | IgM | IgG1 | IgG2a |
| Ex. 1 | 42.0 | −8.0 | 1.6 | 4.6 |
| Ex. 15 | 23.5 | −5.4 | 9.9 | 4.6 |
| Ex. 19 | 30.6 | 1.2 | 8.0 | 0.9 |
| Ex. 20 | 23.7 | −6.2 | 7.4 | 1.3 |
| Ex. 44 | 26.7 | −4.2 | 8.0 | −2.2 |
| Ex. 77 | 55.8 | 1.2 | −6.3 | −3.9 |
| Ex. 86 | 35.9 | −2.7 | −1.1 | 6.2 |
| Ex. 87 | 30.5 | −0.1 | −3.4 | −8.1 |
| Ex. 88 | 22.7 | −4.2 | −6.9 | 8.6 |
| Ex. 90 | 21.5 | −10.3 | 2.7 | 7.0 |
| Ex. 92 | 61.2 | −8.3 | −4.3 | −6.0 |
| Ex. 94 | 63.4 | −1.6 | 7.0 | 2.8 |
| Ex. 96 | 63.2 | 9.6 | 5.0 | 8.3 |
| Ex. 97 | 30.5 | 1.9 | 5.6 | −9.5 |
| Ex. 98 | 50.1 | −2.6 | 5.4 | −4.1 |
| Ex. 99 | 34.8 | 8.5 | 6.1 | 2.7 |
| Ex. 100 | 23.9 | −9.0 | −4.0 | −5.1 |
| Ex. 105 | 47.7 | 0.5 | −4.2 | −1.8 |
| Ex. 106 | 28.8 | −7.3 | −0.8 | 2.1 |

Compounds obtained in Examples 94, 96, 92, 77, 98 and 105 inhibited IgE production by 63.4%, 63.2%, 61.2%, 55.8%, 50.1% and 47.7%, respectively. No effects were observed on the production of IgG1, IgG2a and IgM.

Preparation Example 1: Tablets

| Compound of Example 2 | 10 mg |
|---|---|
| Crystalline cellulose | 60 mg |
| Lactose | 60 mg |
| Hydroxypropyl cellulose | 18 mg |
| Magnesium stearate | 2 mg |
| Total | 150 mg |

Tablets having the above-described composition were prepared in a manner known per se in the art. Tablets so obtained can be formed into sugar-coated or film-coated tablets as needed.

Preparation Example 2: Capsules

| Compound of Example 2 | 10 mg |
|---|---|
| Light silicic anhydride | 25 mg |
| Lactose | 90 mg |
| Starch | 50 mg |
| Talc | 25 mg |
| Total | 200 mg |

The above-described ingredients were filled in No. 1 capsules, whereby capsules were obtained.

Preparation Example 3: Granules

| Compound of Example 19 | 10 mg |
|---|---|
| Lactose | 640 mg |
| Corn starch | 200 mg |
| Carboxymethylcellulose sodium | 20 mg |
| Hydroxypropylcellulose | 130 mg |
| Total | 1000 mg |

In a manner known per se in the art, the granules having the above composition were prepared.

Preparation Example 4: Powders

| Compound of Example 19 | 10 mg |
|---|---|
| Light silicic anhydride | 20 mg |
| Precipitated calcium carbonate | 10 mg |
| Lactose | 290 mg |
| Starch | 70 mg |
| Total | 400 mg |

In a manner known per se in the art, powders having the above composition were prepared.

Preparation Example 5: Injection

| Compound of Example 20 | 1 mg |
|---|---|
| Hydrogenated castor oil | 85 mg |
| Propylene glycol | 60 mg |
| Dextrose | 50 mg |
| Total | Total quantity: 1 ml |

In a manner known per se in the art, an injection having the above composition was prepared.

Preparation Example 6: Drip infusion

| Compound of Example 33 | 5 mg |
|---|---|
| Dextrose | 5000 mg |
| Anhydrous disodium hydrogen phosphate | 10 mg |
| Citric acid | 14.5 mg |
| Total | Total quantity: 100 ml |

In a manner known per se in the art, drip infusion having the following composition was prepared.

Preparation Example 7: Cream preparation

| | |
|---|---|
| Compound of Example 94 | 50 mg |
| White vaseline | 5 g |
| Medium chain fatty acid triglyceride | 15 g |
| Glycerin monostearate | 3.4 g |
| Polyoxyethylene cetyl ether (25E.O.) | 1.6 g |
| Methyl paraoxybenzoate | 0.2 g |
| Butyl paraoxybenzoate | 0.1 g |
| Sodium edatate | 0.02 g |

Purified water was added to give a total amount of 100 g.

In a manner known per se in the art, a cream preparation was prepared using the above ingredients in the above amounts, respectively.

Preparation Example 8: Ointment

| | |
|---|---|
| Compound of Example 105 | 50 mg |
| Diethyl sebacate | 5 g |
| Sesquioleic acid sorbitan | 3 g |
| Purified water | 3 g |
| Sodium edatate | 0.02 g |

White vaseline was added to give a total amount of 100 g.

In a manner known per se in the art, an ointment was prepared using the above ingredients in the above amounts, respectively.

Capability of Exploitation in Industry

Pyridine derivatives (1) of the present invention or salts thereof specifically suppress the production of cytokine and are therefore useful as a cytokine production suppressant or an immunoregulator, more specifically, as a rejection inhibitor upon organ transplantation or as an effective ingredient of the preventive and/or therapeutic for the cytokine-production-induced diseases, particularly immunodysfunction-induced diseases, for example, autoimmune diseases such as allergy, atopy and rheumatism, bronchial asthma, IgA glomerulonephritis, osteoporosis, inflammation, cancers and HIV infection.

What is claimed is:

1. 4,5-Dimethoxy-2-(3-oxo-3-phenyl-1-propenyl) pyridine.

2. A pharmaceutical composition comprising a pyridine derivative or salt thereof, and a pharmaceutically acceptable carrier, wherein the pyridine derivative is represented by the following formula (1):

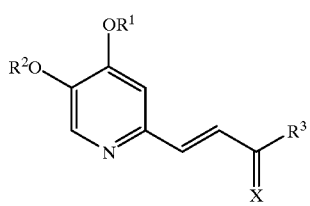

(1)

wherein $R^1$ and $R^2$ are the same or different and each independently represents a hydrogen atom, an alkyl group, a hydroxyalkyl group, an alkoxyalkyl group which may have a substituent, a carboxyalkyl group, an alkoxycarbonylalkyl group, an aralkyl group which may have a substituent, a phenacyl group or an acyl group, $R^3$ represents an alkyl group, or a phenyl group which may have a substituent, and X represents an oxygen atom or combination of a hydroxyl group and a hydrogen atom.

3. The pharmaceutical composition according to claim 2, wherein the pyridine derivative or salt thereof is present in cytokine production suppressant effective amounts.

4. The pharmaceutical composition according to claim 2, wherein the pyridine derivative or salt thereof is present in immunoregulator effective amounts.

5. A method for treatment of diseases induced by the production of cytokine, which comprises administering to a patient an effective amount of a pyridine derivative or salt thereof, wherein said pyridine derivative is represented by the following formula (1):

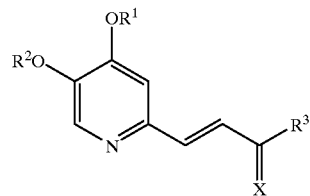

(1)

wherein $R^1$ and $R^2$ are the same or different and each independently represents a hydrogen atom, an alkyl group, a hydroxyalkyl group, an alkoxyalkyl group which may have a substituent, a carboxyalkyl group, an alkoxycarbonylalkyl group, an aralkyl group which may have a substituent, a phenacyl group or an acyl group, $R^3$ represents an alkyl group, or a phenyl group which may have a substituent, and X represents an oxygen atom or combination of a hydroxyl group and a hydrogen atom.

6. A method for treatment of immune disorders, which comprises administering to a patient an effective amount of a pyridine derivative or salt thereof, wherein the pyridine derivative is represented by the following formula (1):

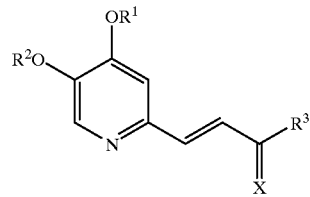

(1)

wherein $R^1$ and $R^2$ are the same or different and each independently represents a hydrogen atom, an alkyl group, a hydroxyalkyl group, an alkoxyalkyl group which may have a substituent, a carboxyalkyl group, an alkoxycarbonylalkyl group, an aralkyl group which may have a substituent, a phenacyl group or an acyl group, $R^3$ represents an alkyl group, or a phenyl group which may have a substituent, and X represents an oxygen atom or combination of a hydroxyl group and a hydrogen atom.

* * * * *